(12) United States Patent
Nalagatla

(10) Patent No.: US 11,992,218 B2
(45) Date of Patent: May 28, 2024

(54) METAL INJECTION MOLDED ANVIL FOR CIRCULAR SURGICAL STAPLER

(71) Applicant: Cilag GmbH International, Zug (CH)

(72) Inventor: Anil K. Nalagatla, Mason, OH (US)

(73) Assignee: Cilag GmbH International, Zug (CH)

( * ) Notice: Subject to any disclaimer, the term of this patent is extended or adjusted under 35 U.S.C. 154(b) by 185 days.

(21) Appl. No.: 17/503,425

(22) Filed: Oct. 18, 2021

(65) Prior Publication Data

US 2023/0117309 A1 Apr. 20, 2023

(51) Int. Cl.
| | |
|---|---|
| *A61B 17/064* | (2006.01) |
| *A61B 17/11* | (2006.01) |
| *A61B 17/115* | (2006.01) |
| *A61B 17/00* | (2006.01) |

(52) U.S. Cl.
CPC ....... *A61B 17/1155* (2013.01); *A61B 17/1114* (2013.01); *A61B 2017/00526* (2013.01); *A61B 2017/1132* (2013.01); *A61B 2017/1135* (2013.01); *A61B 2017/1139* (2013.01)

(58) Field of Classification Search
CPC .......................................... A61B 2017/00526
See application file for complete search history.

(56) References Cited

U.S. PATENT DOCUMENTS

| | | |
|---|---|---|
| 4,119,258 A | 10/1978 | Ewig, Jr. |
| 4,184,620 A | 1/1980 | Ewig |
| 4,224,267 A | 9/1980 | Lugosi et al. |
| 4,706,866 A | 11/1987 | Ebihara |
| 4,813,143 A | 3/1989 | Scheminger et al. |
| 5,163,945 A | 11/1992 | Ortiz et al. |
| 5,205,459 A | 4/1993 | Brinkerhoff et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,297,746 A | 3/1994 | McBride et al. |
| 5,308,576 A | 5/1994 | Green et al. |
| 5,333,773 A | 8/1994 | Main et al. |
| 5,342,373 A | 8/1994 | Stefanchik et al. |
| 5,350,104 A | 9/1994 | Main et al. |

(Continued)

FOREIGN PATENT DOCUMENTS

| | | |
|---|---|---|
| CN | 104107078 A | 10/2014 |
| EP | 0589454 A2 | 3/1994 |

(Continued)

OTHER PUBLICATIONS

European Search Report, Partial, and Provisional Written Opinion dated Mar. 12, 2020, for Application No. 19220044.2, 12 pages.

(Continued)

*Primary Examiner* — Eyamindae C Jallow
(74) *Attorney, Agent, or Firm* — Frost Brown Todd LLP

(57) ABSTRACT

A method is used to manufacture an anvil of a circular surgical stapler. The anvil includes a head and a coupling feature that extends proximally from the head. The method includes forming each of the head and the coupling feature using at least one metal injection molding process. The method also includes after forming the coupling feature, machining a through bore into the coupling feature that extends completely through the coupling feature along a longitudinal axis of the coupling feature.

20 Claims, 22 Drawing Sheets

(56) References Cited

U.S. PATENT DOCUMENTS

| | | | |
|---|---|---|---|
| 5,364,001 A | 11/1994 | Bryan | |
| 5,403,312 A | 4/1995 | Yates et al. | |
| 5,409,276 A | 4/1995 | Engasser | |
| 5,431,668 A | 7/1995 | Burbank, III et al. | |
| 5,445,167 A | 8/1995 | Yoon et al. | |
| 5,487,499 A | 1/1996 | Sorrentino et al. | |
| 5,533,661 A | 7/1996 | Main et al. | |
| 5,584,845 A | 12/1996 | Hart | |
| 5,601,573 A | 2/1997 | Fogelberg et al. | |
| 5,722,306 A | 3/1998 | Vela et al. | |
| 5,807,338 A | 9/1998 | Smith et al. | |
| 5,951,574 A | 9/1999 | Stefanchik et al. | |
| 6,176,021 B1 | 1/2001 | Sato et al. | |
| 6,185,771 B1 | 2/2001 | Trusty, Sr. | |
| 6,269,714 B1 | 8/2001 | Sakai | |
| 6,959,851 B2 | 11/2005 | Heinrich | |
| 6,988,650 B2 | 1/2006 | Schwemberger et al. | |
| 7,000,818 B2 | 2/2006 | Shelton, IV et al. | |
| 7,043,819 B1 | 5/2006 | Arnold | |
| 7,134,587 B2 | 11/2006 | Schwemberger et al. | |
| 7,147,140 B2 | 12/2006 | Wukusick et al. | |
| 7,195,631 B2 | 3/2007 | Dumbauld | |
| 7,204,404 B2 | 4/2007 | Nguyen et al. | |
| 7,207,472 B2 | 4/2007 | Wukusick et al. | |
| 7,261,724 B2 | 8/2007 | Molitor et al. | |
| 7,380,696 B2 | 6/2008 | Shelton, IV et al. | |
| 7,422,139 B2 | 9/2008 | Shelton, IV et al. | |
| 7,464,849 B2 | 12/2008 | Shelton, IV et al. | |
| 7,670,334 B2 | 3/2010 | Hueil et al. | |
| 7,686,820 B2 | 3/2010 | Huitema et al. | |
| 7,699,860 B2 | 4/2010 | Huitema et al. | |
| 7,731,724 B2 | 6/2010 | Huitema et al. | |
| 7,753,245 B2 | 7/2010 | Boudreaux et al. | |
| 7,771,425 B2 | 8/2010 | Dycus et al. | |
| 7,845,537 B2 | 12/2010 | Shelton, IV et al. | |
| 7,980,443 B2 | 7/2011 | Scheib et al. | |
| 8,008,598 B2 | 8/2011 | Whitman et al. | |
| 8,021,389 B2 | 9/2011 | Molz, IV | |
| 8,038,686 B2 | 10/2011 | Huitema et al. | |
| 8,087,562 B1 | 1/2012 | Manoux et al. | |
| 8,210,411 B2 | 7/2012 | Yates et al. | |
| 8,220,688 B2 | 7/2012 | Laurent et al. | |
| 8,262,679 B2 | 9/2012 | Nguyen | |
| 8,308,040 B2 | 11/2012 | Huang et al. | |
| 8,393,514 B2 | 3/2013 | Shelton, IV et al. | |
| 8,408,439 B2 | 4/2013 | Huang et al. | |
| 8,453,914 B2 | 6/2013 | Laurent et al. | |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 8,770,458 B2 | 7/2014 | Scirica | |
| 8,910,847 B2 | 12/2014 | Nalagatla et al. | |
| 9,072,535 B2 | 7/2015 | Shelton, IV et al. | |
| 9,101,358 B2 | 8/2015 | Kerr et al. | |
| 9,186,142 B2 | 11/2015 | Fanelli et al. | |
| 9,192,383 B2 | 11/2015 | Milliman | |
| 9,345,481 B2 | 5/2016 | Hall et al. | |
| 9,517,065 B2 | 12/2016 | Simms et al. | |
| 9,713,469 B2 | 7/2017 | Leimbach et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,867,615 B2 | 1/2018 | Fanelli et al. | |
| 9,907,552 B2 | 3/2018 | Measamer et al. | |
| 9,936,949 B2 | 4/2018 | Measamer et al. | |
| 10,092,292 B2 | 10/2018 | Boudreaux et al. | |
| 10,478,189 B2 | 11/2019 | Bear et al. | |
| 10,687,814 B2 | 6/2020 | Dunki-Jacobs | |
| 10,695,068 B2 | 6/2020 | Kluener et al. | |
| 10,709,452 B2 | 7/2020 | DiNardo et al. | |
| 10,729,444 B2 | 8/2020 | Stager et al. | |
| 11,103,245 B2 | 8/2021 | Nalagatla et al. | |
| 11,291,450 B2 | 4/2022 | Nalagatla et al. | |
| 2005/0004568 A1 | 1/2005 | Lawes et al. | |
| 2005/0139636 A1 | 6/2005 | Schwemberger et al. | |
| 2005/0143759 A1 | 6/2005 | Kelly | |
| 2005/0145672 A1 | 7/2005 | Schwemberger et al. | |
| 2005/0149087 A1 | 7/2005 | Ahlberg et al. | |
| 2006/0047309 A1 | 3/2006 | Cichocki, Jr. | |
| 2006/0090603 A1 | 5/2006 | Lewis et al. | |
| 2006/0219752 A1 | 10/2006 | Arad et al. | |
| 2007/0056932 A1 | 3/2007 | Whitman et al. | |
| 2007/0082229 A1 | 4/2007 | Mirchandani et al. | |
| 2007/0169605 A1 | 7/2007 | Szymanski | |
| 2007/0175955 A1 | 8/2007 | Shelton, IV et al. | |
| 2008/0078800 A1 | 4/2008 | Hess et al. | |
| 2008/0142187 A1 | 6/2008 | Jadeed et al. | |
| 2008/0308605 A1 | 12/2008 | Scirica | |
| 2009/0001128 A1 | 1/2009 | Weisenburgh, II et al. | |
| 2010/0127039 A1 | 5/2010 | Hessler | |
| 2010/0249807 A1 | 9/2010 | Chen et al. | |
| 2011/0068147 A1 | 3/2011 | Racenet et al. | |
| 2012/0116422 A1 | 5/2012 | Triplett et al. | |
| 2012/0203339 A1* | 8/2012 | Heaven | A61F 2/0805 623/13.14 |
| 2012/0292366 A1 | 11/2012 | Nalagatla et al. | |
| 2012/0292371 A1 | 11/2012 | Nalagatla et al. | |
| 2012/0292372 A1 | 11/2012 | Nalagatla et al. | |
| 2013/0256382 A1 | 10/2013 | Swayze et al. | |
| 2014/0239037 A1 | 8/2014 | Boudreaux et al. | |
| 2014/0263552 A1 | 9/2014 | Hall et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2016/0374672 A1 | 12/2016 | Bear et al. | |
| 2017/0027571 A1 | 2/2017 | Nalagatla et al. | |
| 2017/0258471 A1 | 9/2017 | DiNardo et al. | |
| 2017/0265867 A1 | 9/2017 | Nativ et al. | |
| 2018/0056095 A1 | 3/2018 | Messerly et al. | |
| 2018/0085932 A1 | 3/2018 | Yu Chen | |
| 2018/0132849 A1 | 5/2018 | Miller et al. | |
| 2018/0132853 A1 | 5/2018 | Miller et al. | |
| 2018/0310938 A1 | 11/2018 | Kluener et al. | |
| 2018/0310939 A1 | 11/2018 | Stager et al. | |
| 2018/0368839 A1 | 12/2018 | Shelton, IV et al. | |
| 2018/0368840 A1 | 12/2018 | Shelton, IV et al. | |
| 2018/0368842 A1 | 12/2018 | Shelton, IV et al. | |
| 2018/0368843 A1 | 12/2018 | Shelton, IV et al. | |
| 2019/0046193 A1 | 2/2019 | Dunki-Jacobs et al. | |
| 2019/0090875 A1 | 3/2019 | Fox et al. | |
| 2019/0216561 A1 | 7/2019 | Manzo et al. | |
| 2019/0254679 A1 | 8/2019 | Russell | |
| 2019/0341753 A1 | 11/2019 | Nemoto et al. | |
| 2020/0054322 A1 | 2/2020 | Harris et al. | |
| 2020/0054323 A1 | 2/2020 | Harris et al. | |
| 2020/0205815 A1 | 7/2020 | Nalagatla et al. | |
| 2020/0205835 A1 | 7/2020 | Nalagatla et al. | |
| 2020/0206805 A1 | 7/2020 | Nalagatla et al. | |

FOREIGN PATENT DOCUMENTS

| | | | |
|---|---|---|---|
| EP | 2215977 A2 * | 8/2010 | ......... A61B 17/0644 |
| EP | 3241506 A1 | 11/2017 | |
| EP | 3323358 A1 | 5/2018 | |
| EP | 3673835 A2 * | 7/2020 | ......... A61B 17/1155 |
| WO | WO 2016/179737 A1 | 11/2016 | |
| WO | WO 2017/197594 A1 | 11/2017 | |
| WO | WO-2019003030 A1 * | 1/2019 | ....... A61B 17/07207 |

OTHER PUBLICATIONS

European Search Report, Extended, and Written Opinion dated Jul. 15, 2020, for Application No. 19220044.2, 14 pages.

European Search Report, Partial, and Provisional Written Opinion dated Apr. 29, 2020, for Application No. 19219993.3, 11 pages.

European Search Report, Extended, and Written Opinion dated Aug. 7, 2020, for Application No. 19219993.3, 12 pages.

International Search Report and Written Opinion dated Jun. 15, 2020, for International Application No. PCT/IB2019/060817, 18 pages.

(56) References Cited

OTHER PUBLICATIONS

International Search Report and Written Opinion dated Jun. 23, 2020, for International Application No. PCT/IB2019/060822, 17 pages.
International Search Report and Written Opinion dated Mar. 6, 2023, for International Application No. PCT/IB2022/059918, 21 pages.

* cited by examiner

METAL INJECTION MOLDED ANVIL FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular surgical stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular surgical stapler may be configured to sever the tissue and seal the tissue substantially simultaneously. For instance, the circular surgical stapler may sever excess tissue that is interior to an annular array of staples at an anastomosis, to provide a substantially smooth transition between the anatomical lumen sections that are joined at the anastomosis. Circular surgical staplers may be used in open procedures or in endoscopic procedures. In some instances, a portion of the circular surgical stapler is inserted through a patient's naturally occurring orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of which is incorporated by reference herein.

Some circular surgical staplers may include a motorized actuation mechanism. Examples of circular surgical staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; and U.S. Pat. No. 9,713,469, entitled "Surgical Stapler with Rotary Cam Drive," issued Jul. 25, 2017. The disclosure of each of the which is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
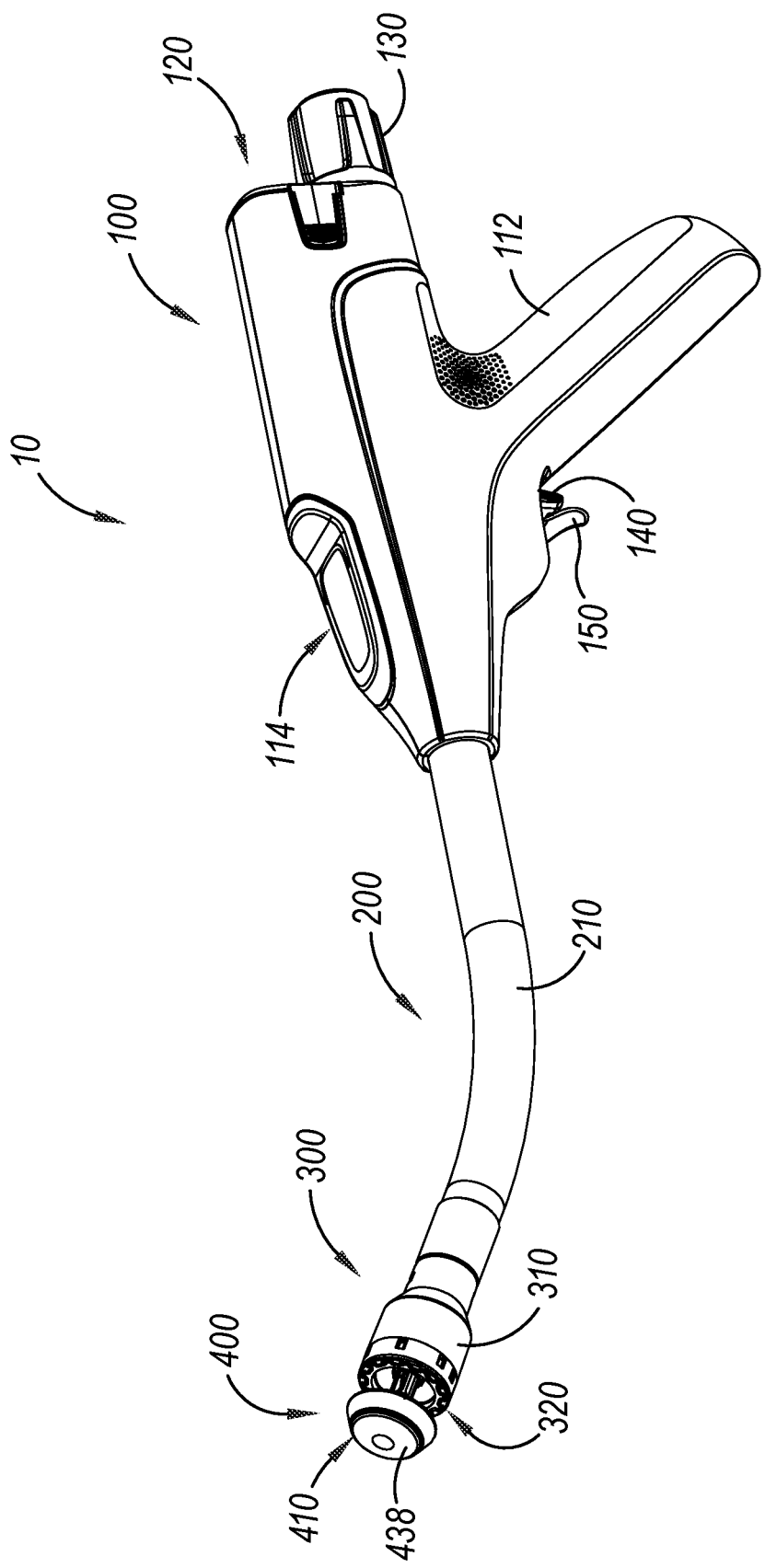
FIG. 1 depicts a perspective view of an exemplary circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. Overview of Exemplary Circular Stapling Surgical Instrument

A. Exemplary Circular Stapling Surgical Instrument

Figure 2:
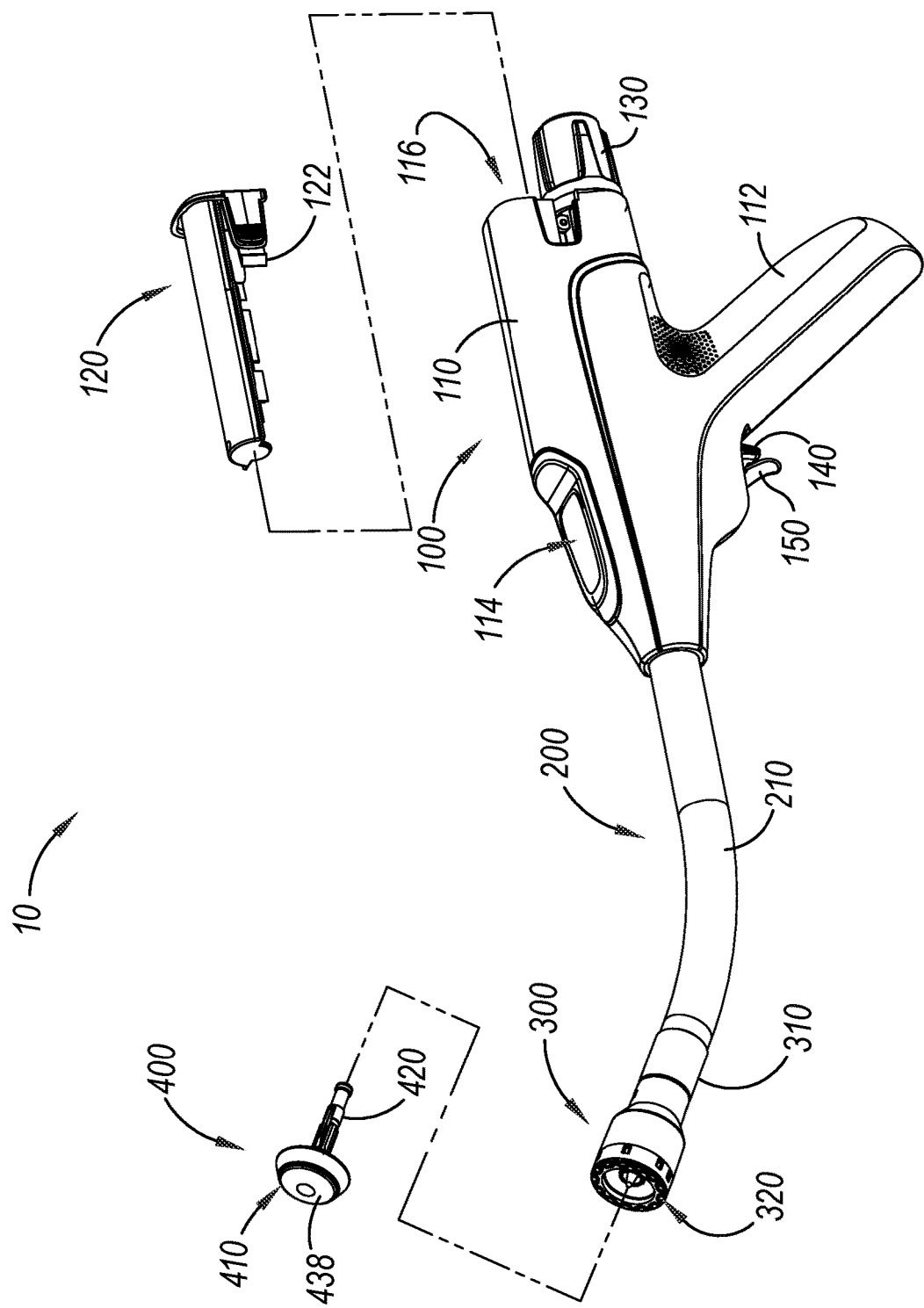
FIG. 2 depicts a perspective view of the circular surgical stapler of FIG. 1, with a battery pack removed from a handle assembly and an anvil removed from a stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (100) further includes a user feedback feature (114) that permits viewing of a movable indicator needle (not shown).

Instrument (10) includes a battery pack (120). Battery pack (120) is operable to provide electrical power to a motor (160) in pistol grip (112). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. It should be understood that battery pack (120) and handle assembly (100) may have complementary electrical contacts, pins and sockets, and/or other features that provide paths for electrical communication from battery pack (120) to electrically powered components in handle assembly (100). Shaft assembly (200) extends distally from handle assembly (100) and includes a preformed bend, which may facilitate positioning of stapling head assembly (300) within a patient's colon.

Stapling head assembly (300) is located at the distal end of shaft assembly (200). As shown in FIGS. 1-2, anvil (400) is configured to removably couple with shaft assembly (200), adjacent to stapling head assembly (300). Anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to provide cutting and stapling of the tissue.

B. Exemplary Anvil

Figure 3:
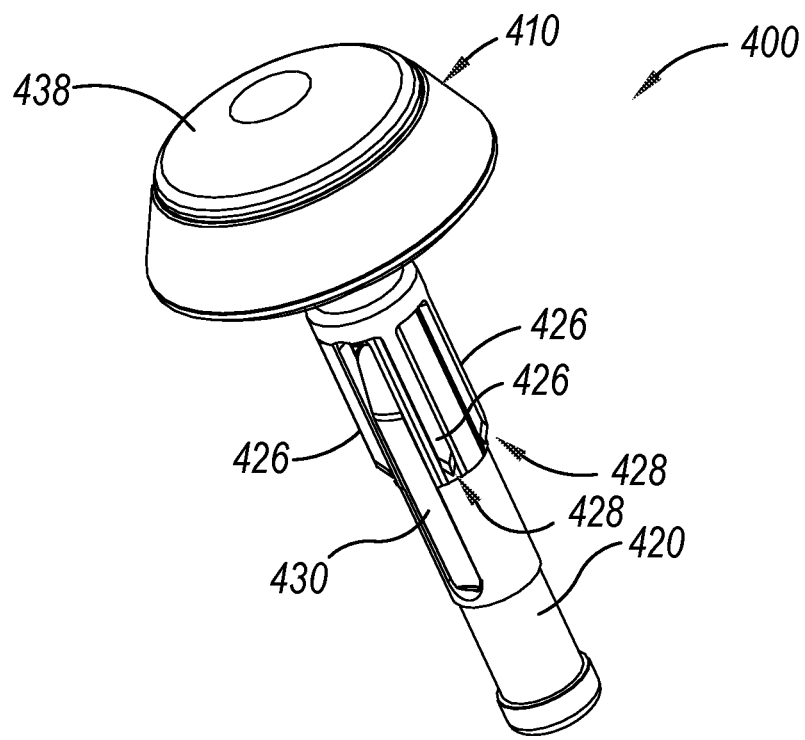
FIG. 3 depicts a perspective view of the anvil of the circular surgical stapler of FIG. 1.
Figure 4:
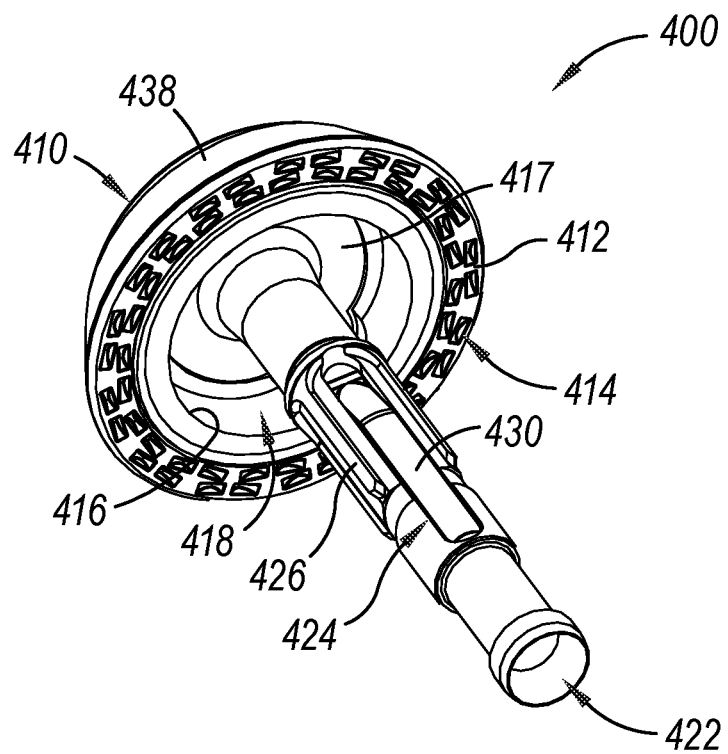
FIG. 4 depicts another perspective view of the anvil of FIG. 3.
Figure 5:
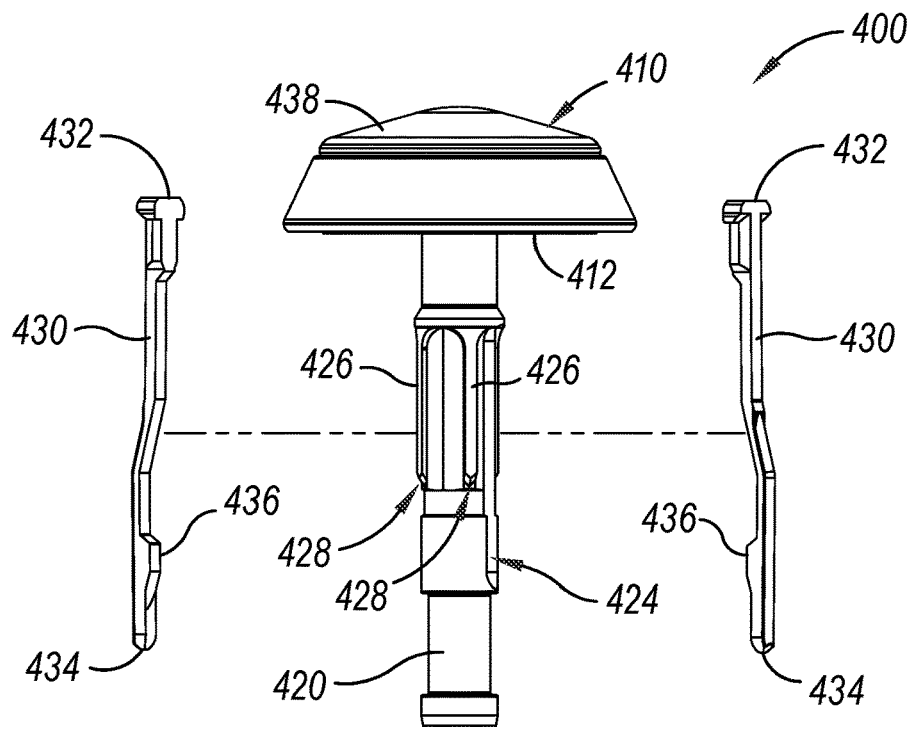
FIG. 5 depicts an exploded side elevational view of the anvil of FIG. 3.

As shown in FIGS. 3-5, anvil (400) includes a head (410) and a shank (420). Head (410) includes a proximal surface (412) that defines an annular array of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Latch members (430) are configured to resiliently bias distal ends (434) and latch shelves (436) to pivot radially inwardly toward the longitudinal axis defined by shank (420). Latch members (430) thus act as retaining clips. This allows anvil (400) to be removably secured to an anvil coupling feature of stapling head assembly (300) in the form of a trocar (330). When shank (420) is secured to trocar (330) and trocar (330) is retracted proximally, the inner diameter of bore (314) in inner core member (312) of body member (310) laterally constrains latch members (430) to maintain engagement between latch shelves (436) and proximal surface (338) of head (334) of trocar (330). This engagement prevents anvil (400) from being released from trocar (330) during firing of stapling head assembly (300). It should be understood, however, that latch shelves (436) are merely optional. Anvil (400) may be removably secured to a trocar (330) using any other suitable components, features, or techniques. In some versions, stapling head assembly (300) may include an actuatable first coupling feature that is similar in structure to shank (420), and anvil (400) may include a second coupling feature that is similar in structure to trocar (330) and is configured to releasably couple with the first coupling feature. As shown in FIG. 4, anvil (400) of the present example includes a breakable washer (417) within annular recess (418). This washer (417) is broken by knife member (340) when the knife member (340) completes a full distal range of motion.

As shown in FIGS. 3-4, shank (420) includes a set of longitudinally extending splines (426) that are spaced about shank (420) in an angular array. The proximal end of each spline (426) includes a respective lead-in edge (428). Splines (426) are configured to engage corresponding splines (316) of an inner body member (310) of stapling head assembly (300) in order to consistently provide a predetermined angular alignment between anvil (400) and stapling head assembly (300). This angular alignment may ensure that staple forming pockets (414) of anvil (400) are consistently angularly aligned appropriately with staple openings (324) of stapling head assembly (300).

C. Exemplary Stapling Head Assembly

Figure 6:
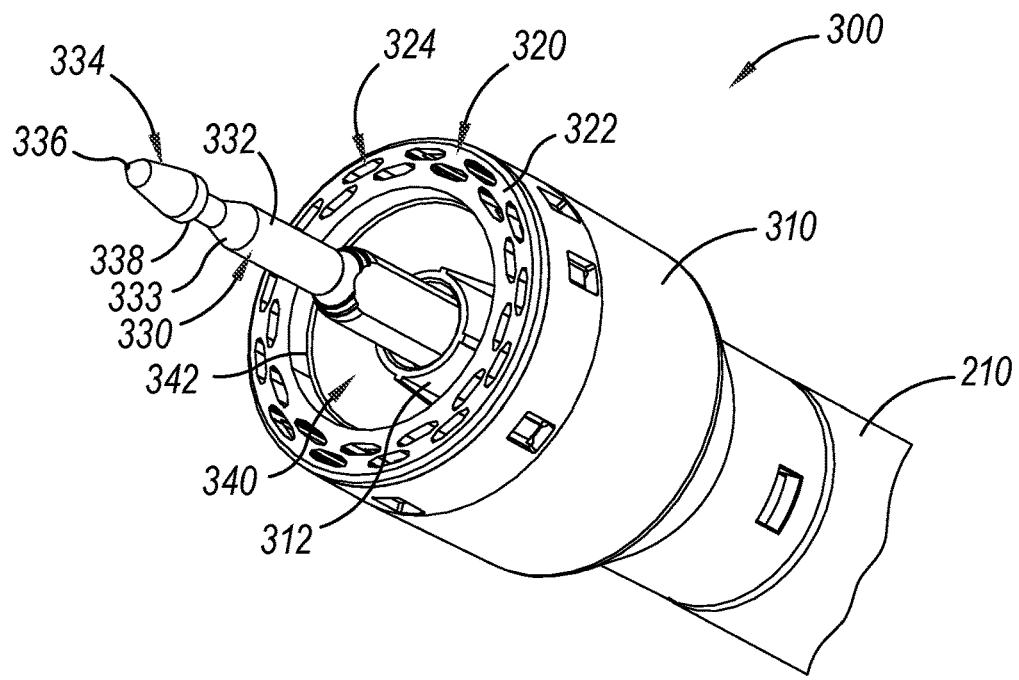
FIG. 6 depicts a perspective view of the stapling head assembly of the circular surgical stapler of FIG. 1.

As shown in FIG. 6, stapling head assembly (300) of the present example is coupled to a distal end of shaft assembly (200) and comprises a body member (310) and a slidable staple driver member (not shown). Body member (310) includes a distally extending cylindraceous inner core member (312). Body member (310) is fixedly secured to an outer sheath (210) of shaft assembly (200). Body member (310) and outer sheath (210) thus serve together as a mechanical ground for stapling head assembly (300).

Figure 7:
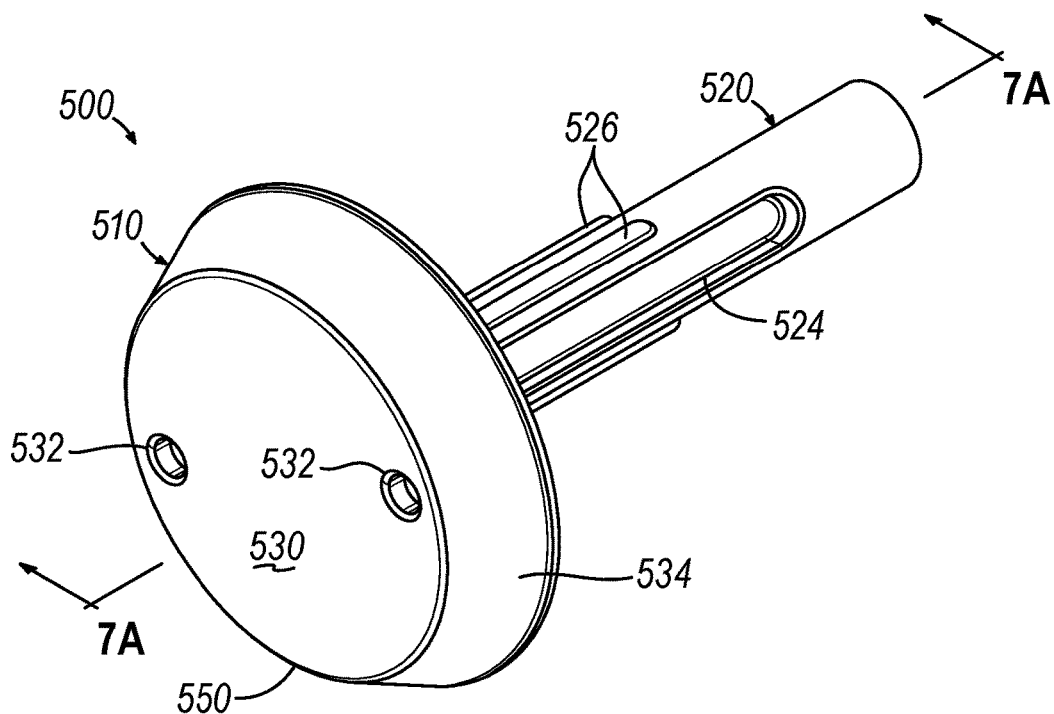
FIG. 7 depicts a perspective view of a first exemplary alternative anvil after forming a first exemplary alternative head together with a first exemplary alternative shank, where the anvil may be incorporated into the circular surgical stapler of FIG. 1.

With continued reference to FIG. 7, inner core member (312) of body member (310) defines a bore (314). A plurality of longitudinally extending splines (not shown) are spaced in an angular array within bore (314). The distal ends of splines (not shown) include lead-in edges that are configured to complement lead-in edges (428) of splines (426) on shank (420) of anvil (400). In particular, after shank (420) is secured to trocar (330), and as anvil (400) is thereafter retracted proximally relative to stapling head assembly (300), lead-in edges (428) may cooperatively engage lead-in edges (not shown) to drive anvil (400) to rotate relative to trocar (330) to angularly align splines (426) of anvil (400) with the gaps between corresponding splines (not shown)) of body member (310). In this manner, when splines (426) of anvil (400) are positioned within the gaps between splines (not shown) of body member (310), anvil (400) may achieve a predetermined angular alignment relative to stapling head assembly (300). This predetermined angular alignment may ensure that staple openings (324) of deck member (320) are precisely aligned with corresponding staple forming pockets (414) of anvil (400). Thus, splines (426) are configured to ensure that staples ejected through staple openings (324) are accurately driven into corresponding staple forming pockets (414) on a consistent basis, regardless of the angular orientation of anvil (400) relative to stapling head assembly (300) at the time anvil (400) is initially secured to trocar (330).

Trocar (330) is positioned coaxially within inner core member (312) of body member (310). Trocar (330) may include a colored region (333). Trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430). Knife member (340) includes a distally presented, sharp circular cutting edge (342).

A deck member (320) is fixedly secured to body member (310). Deck member (320) includes a distally presented deck surface (322) defining two concentric annular arrays of staple openings (324). Staple openings (324) are arranged to correspond with the arrangement of staple drivers and staple forming pockets (414). Thus, each staple opening (324) is configured to provide a path for a corresponding staple driver to drive a corresponding staple through deck member (320) and into a corresponding staple forming pocket (414) when stapling head assembly (300) is actuated. Deck member (320) is thus configured to allow knife member (340) to translate distally to a point where cutting edge (342) is distal to deck surface (322).

II. Exemplary Anvils and Methods of Manufacture

As described above, anvil (400) of instrument (10) may be machined as a single unitary component or anvil (400) may be manufactured by initially forming head (410) and shank (420) as separate pieces and then later joining head (410) and shank (420) together. In instances in which head (410) and shank (420) are initially formed as separate pieces, it may be desirable to strengthen the coupling between head (410) and shank (420). Additionally, it may be desirable to make head (410) and shank (420) using different manufacturing processes and in a low-cost manner. Moreover, it may be desirable to refine certain portions and surfaces of head (410) and/or shank (420) to improve the operability of anvil (400) with instrument (10). Therefore, it may be desirable to manufacture exemplary anvils (500b, 700b, 900a, 1100b, 1300a) that provide such characteristics while also enabling anvils (500b, 700b, 900a, 1100b, 1300a) to function interchangeably with anvil (400) described above with reference to FIGS. 1-5. It is envisioned that one or more aspects of anvils (500b, 700b, 900a, 1100b, 1300a) may be combined with one or more aspects of U.S. Pub. No. 2020/0205835, entitled "Anvil for Circular Surgical Stapler and Associated Method of Manufacture with MIM," published Jul. 2, 2020, and issued as U.S. Pat. No. 11,291,450 on Apr. 5, 2022, the disclosure of which is incorporated by reference herein.

As will be described with reference to FIGS. 7-33, instrument (10) includes anvil (500b, 700b, 900a, 1100b, 1300a), which is intended to be used in place of anvil (400) described above with reference to FIGS. 1-5. As will be described in greater detail below, and similar to the functionality of anvil (400), each of anvils (500b, 700b, 900a, 1100b, 1300a) is configured to couple with trocar (330), or with an alternative actuatable coupling feature of stapling head assembly (300), and each is configured to deform staples driven by the staple driver. Furthermore, it will be appreciated that the exemplary manufacturing methods described below may be similarly employed for variations of anvils (500b, 700b, 900a, 1100b, 1300a) having a coupling feature other than a shank, such as a coupling feature similar in structure to trocar (330).

A. First Exemplary Alternative Anvil and Method of Manufacturing

Figure 8:
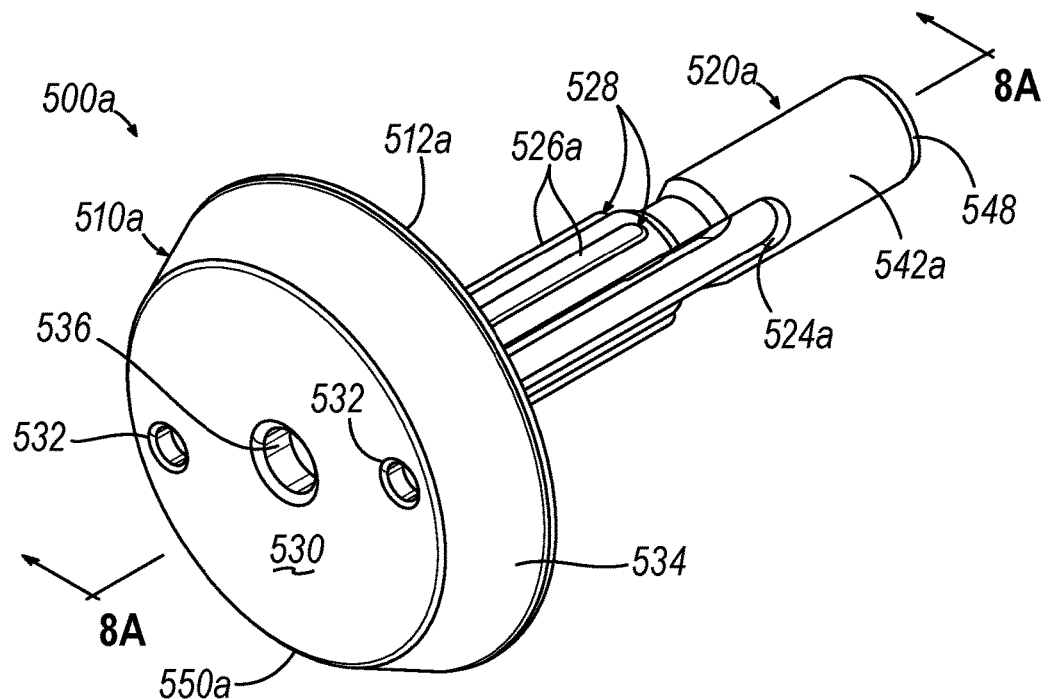
FIG. 8 depicts a perspective view of the anvil of FIG. 7 after another manufacturing step.
Figure 9:
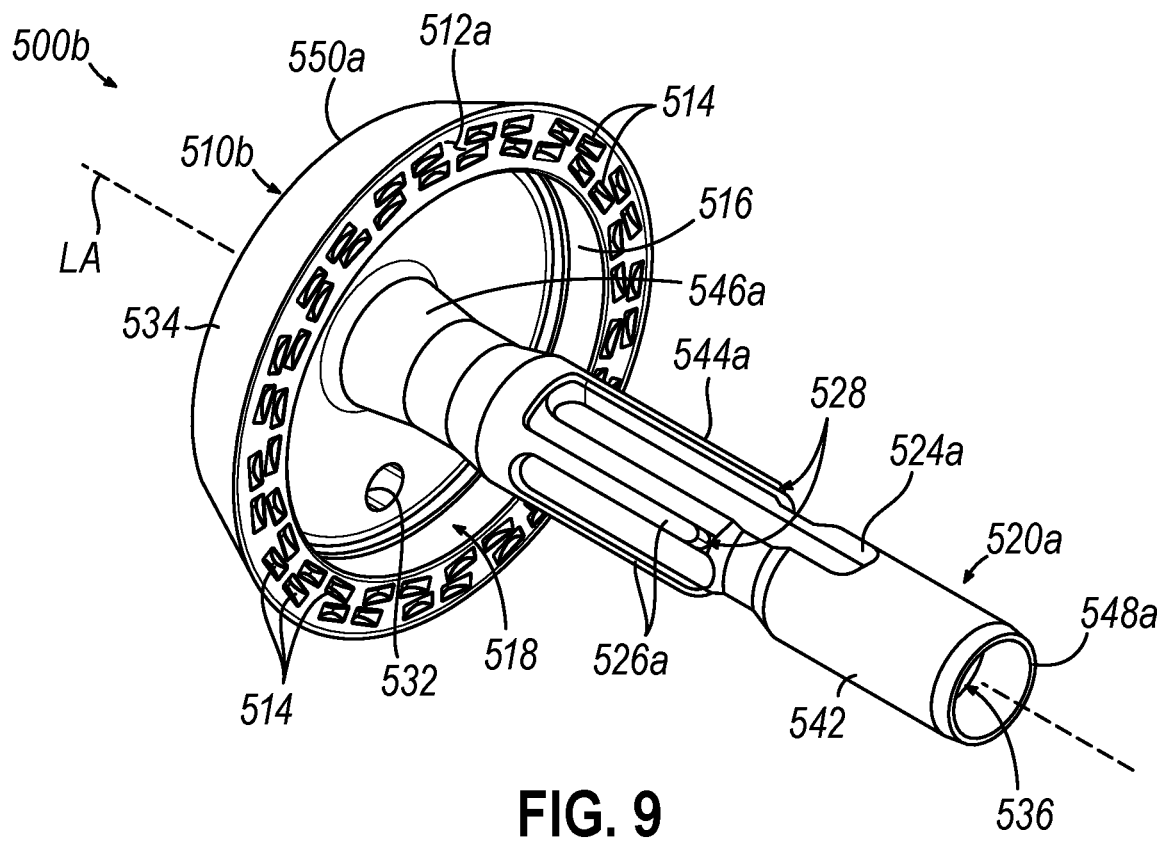
FIG. 9 depicts a perspective view of the anvil of FIG. 8 after another manufacturing step.
Figure 10:
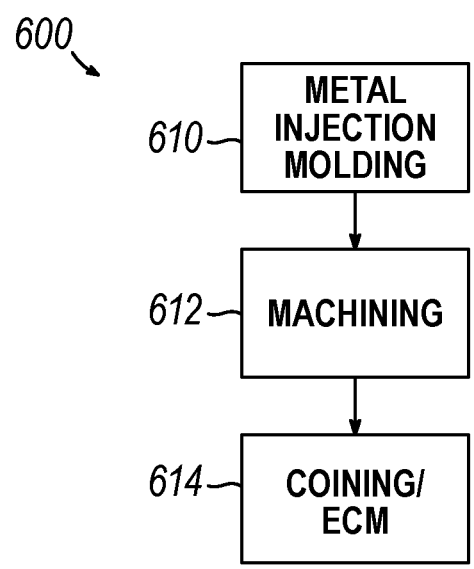
FIG. 10 depicts a diagrammatic view of an exemplary method of manufacturing the anvil of FIG. 9 that may be incorporated into the circular surgical stapler of FIG. 1.

FIGS. 7-9 show a first exemplary alternative anvil (500, 500a, 500b) during various manufacturing stages where completed anvil (500b) may be incorporated into instrument (10) of FIG. 1, and FIG. 10 shows an exemplary method (600) of manufacturing anvil (500b). Anvil (500b) is configured to couple with anvil coupling feature (e.g., trocar (330)), so that anvil (500) is configured to deform staples driven by the staple driver. Anvil (500) includes a head (510) and a shank (520) that extends proximally from head (510).

Figure 7A:
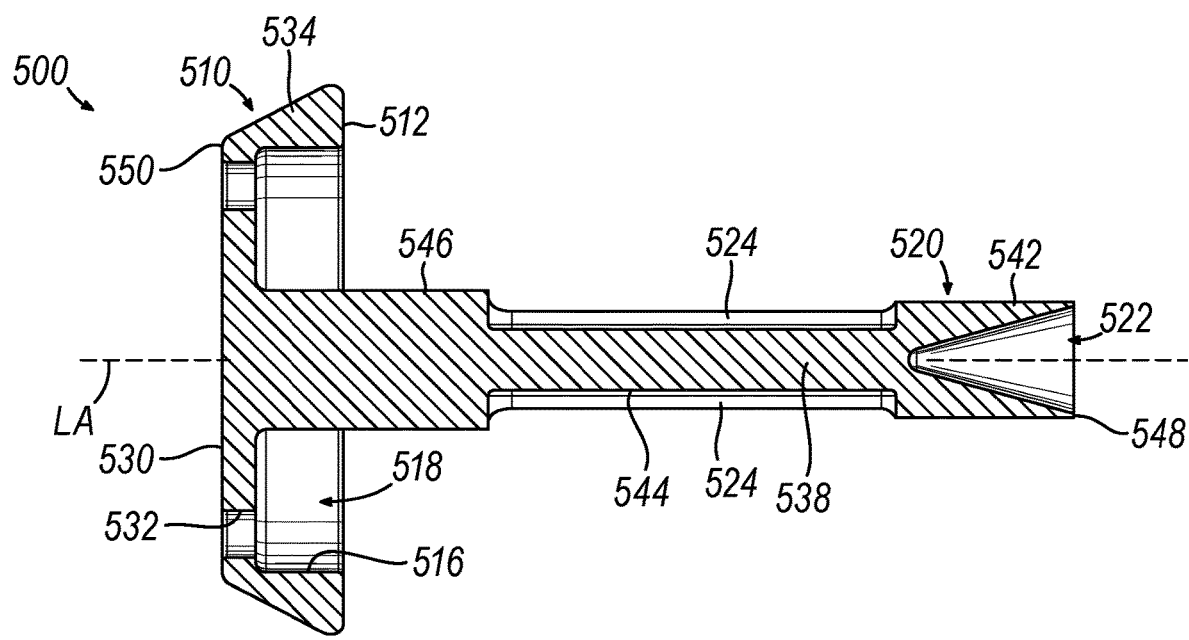
FIG. 7A depicts a sectional view of the anvil of FIG. 7, taken along line 7A-7A of FIG. 7.

Head (510) includes a proximal surface (512), which is shown in FIGS. 7 and 7A without an annular array of staple forming pockets (514), which are formed later as discussed below. Staple forming pockets (514) are shown schematically in FIG. 8A. Proximal surface (512) of head (510) terminates at an inner edge (516), which defines an outer boundary of an annular recess (518) surrounding shank (520). Distal outer surface (530) of head (510) includes one or more apertures (532), with two being shown, that may be used to couple with a cap (not shown), but which may be similar to cap (438). Head (510) also includes a tapered portion (534) extending proximally from distal outer surface (530).

Shank (520) extends along a longitudinal axis (LA) and defines a bore (522). Bore (522) is shown as a conical bore that extends through only a portion of shank (520), which is subsequently refined through one or more machining processes. Similar to shank (420), shank (520) includes a set of longitudinally extending splines (526) that are spaced about shank (520) in an angular array, where the proximal ends of splines (526) include a lead-in edge (528). Lateral openings (524) provide clearance for a latch member (not shown), but which may be similar to latch member (430), to deflect radially outwardly from longitudinal axis (LA) defined by shank (520).

Method (600) includes forming head (510) and shank (520) using at least one metal injection molding process to produce anvil (500) as shown and described above with reference to FIGS. 7 and 7A. In this version, head (510) may be simultaneously formed with shank (520) using the same metal injection molding process. Head (510) and shank (520) are shown as being integrally formed together as a unitary piece. Metal injection molding (MIM) refers to any metalworking process where finely-powdered metal is mixed with a binder material to create a feedstock that is subsequently shaped and solidified using molding process (such as injection molding). The shape and dimensions of anvil (500) may be optimized for the metal injection molding process. For example, shank (520) of FIG. 7A has a generally solid shape (538) except for bore (522) and apertures (532). This generally solid shape (538) may improve the structural integrity of anvil (500) during the metal injection molding process.

Figure 8A:
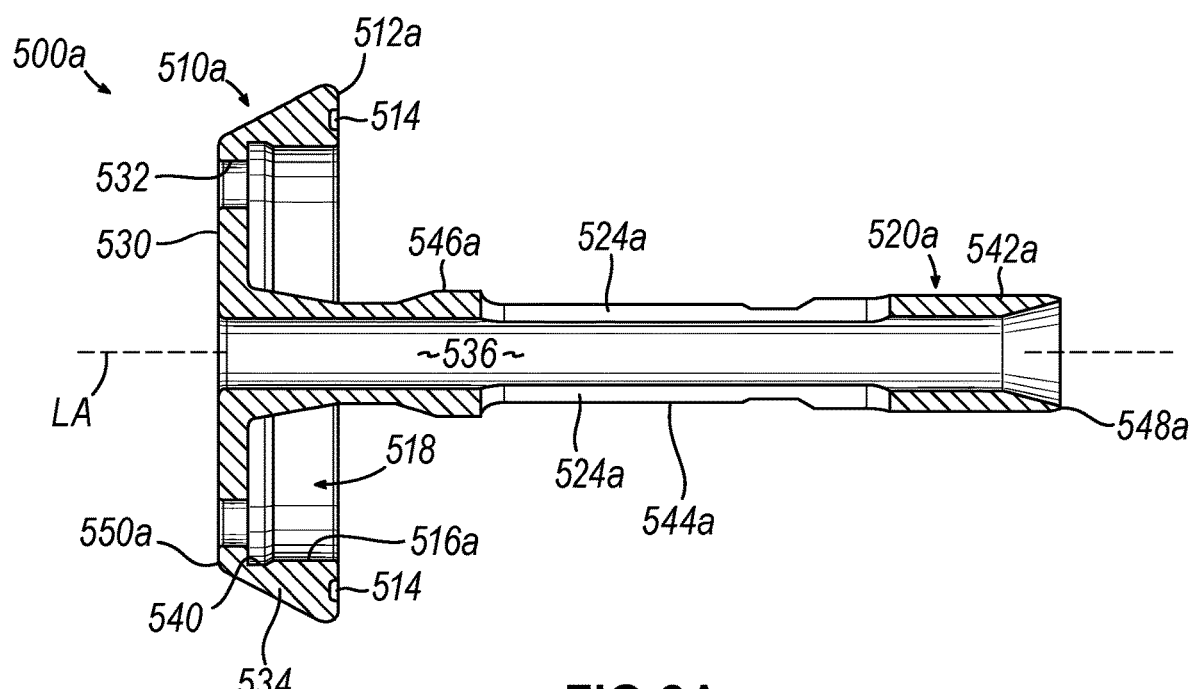
FIG. 8A depicts a sectional view of the anvil of FIG. 8, taken along line 8A-8A of FIG. 8.

As shown in FIGS. 8 and 8A, after forming head (510) and shank (520) using metal injection molding, at step (612), method (600) includes machining select portions of head (510a) and/or shank (520a). Selective machining may reduce the time and cost associated with machining an entirety of anvil (500). As shown by comparing the cross-sections of FIGS. 7A and 8A, a groove (540) may be machined into inner edge (516a) also referred to as an inner side wall of head (510a). Additionally, select portions of proximal, central, and distal portions (542a, 544a, 546a) of shank (520a) may be machined to improve select dimensional tolerances which without machining anvil (500a) in its entirety. A through bore (536) is machined into shank (520) so as to extend completely through longitudinal axis (LA) of shank (520). In other words, through bore (536) extends from a tapered proximal end (548) of shank (520) to a distal end (550a) of head (510). Additionally, distal end (548a) may be machined to include a taper.

Splines (526a) and lateral openings (524a) may be refined through one or more machining processes. For example, lead-in edges (528) of splines (526a) may be machined into shank (520). Splines (526a) are configured to align with features of instrument (10). Splines (526a) are configured to engage corresponding splines (not shown) of inner body member (310) of stapling head assembly (300) to consistently provide a predetermined angular alignment between anvil (500) and stapling head assembly (300). This angular alignment may ensure that staple forming pockets (514) of anvil (500) are consistently angularly aligned appropriately with staple openings (324) of stapling head assembly (300). Thus, splines (526a) are precisely and consistently positioned in relation to staple forming pockets (514).

In this version, staple forming pockets (514) are formed into head (510b) of anvil (500b) after metal injection molding head (510). At step (614), method (600) may include coining or electrochemically machining staple forming pockets (514) into proximal surface (512a) of head (510a). While not shown, in some versions, staple forming pockets (514) may be initially formed using one or more machining processes during step (614) whereby coining and/or electrochemically improves select dimensional tolerances of select portions of staple forming pockets (514). As shown in FIG. 9, staple forming pockets (514) are arranged in two concentric annular arrays. Alternatively, staple forming pockets (514) may be arranged in three or more concentric annular arrays. Staple forming pockets (514) are configured to deform the staples as the staples are driven into staple forming pockets (514). For instance, each staple forming pocket (514) may deform a generally "U" shaped staple into a "B" shape as is known in the art. Alternatively, staple forming pockets (514) may be formed using coining or electrochemically machining.

Coining is a form of precision stamping where a workpiece is subjected to a sufficiently high stress so as to induce plastic flow on the surface of the material. The plastic flow reduces surface grain size and work hardens proximal surface (512a), while the material deeper within the workpiece retains its toughness and ductility. Coining also improves the dimensional tolerances of staple forming pocket (514). Electrochemical machining (ECM) is a method of removing metal using one or more electrochemical processes. Electrochemical machining may be used for mass production due to cost effectiveness and is utilized for working extremely hard materials or materials that are difficult to machine using conventional methods. Electrochemical machining may cut small or uniquely-shaped angles, intricate contours, or cavities in hard metals workpieces.

Method (600) may optionally include electropolishing at least a portion of the annular array of staple forming pockets (514). Electropolishing is an electrochemical finishing process that removes a thin layer of material from a metal part. Electropolishing results in a shiny and smooth surface finish. Method (600) may optionally include magnetically deburring or bead blasting anvil (500, 500a, 500b) (e.g., head (510a, 510b)). Magnetic deburring removes light burrs from non-ferrous parts. In magnetic deburring, rotating magnets move small stainless-steel pins around a bowl of the magnetic deburring machine, rubbing the small stainless-steel pins against the portion of anvil (500, 500a, 500b) being deburred.

While not shown, shank (520a) may include a pair of pivoting latch members positioned in bore (522), that may be similar in structure and function to latch members (430) described above with reference to shank (420) of anvil (400). The latch members may be inserted into bore (536) at any time after step (610) of metal injection molding. For example, latch members may be inserted into bore (536) after step (612) of machining anvil (500) or after step (614) of coining or electrochemically machining staple forming pockets (514). The latch members may be positioned within bore (536) such that the distal ends are positioned at the proximal ends of lateral openings (524), which are formed through the sidewall of shank (520a). The latch members allow anvil (500b) to be removably secured to a trocar (330) of stapling head assembly (300). When shank (520a) is secured to trocar (330) and trocar (330) is retracted proximally, the inner diameter of bore (314) in inner core member (312) of inner body member (310) laterally constrains the latch members to maintain engagement with proximal surface (338) of head (334) of trocar (330). This engagement prevents anvil (500b) from being released from trocar (330) during firing of stapling head assembly (300). In some versions, the latch members may be omitted, such that anvil (500b) may be removably secured to a trocar (330) using any other suitable components, features, or techniques.

B. Second Exemplary Alternative Anvil and Method of Manufacturing

Figure 11:
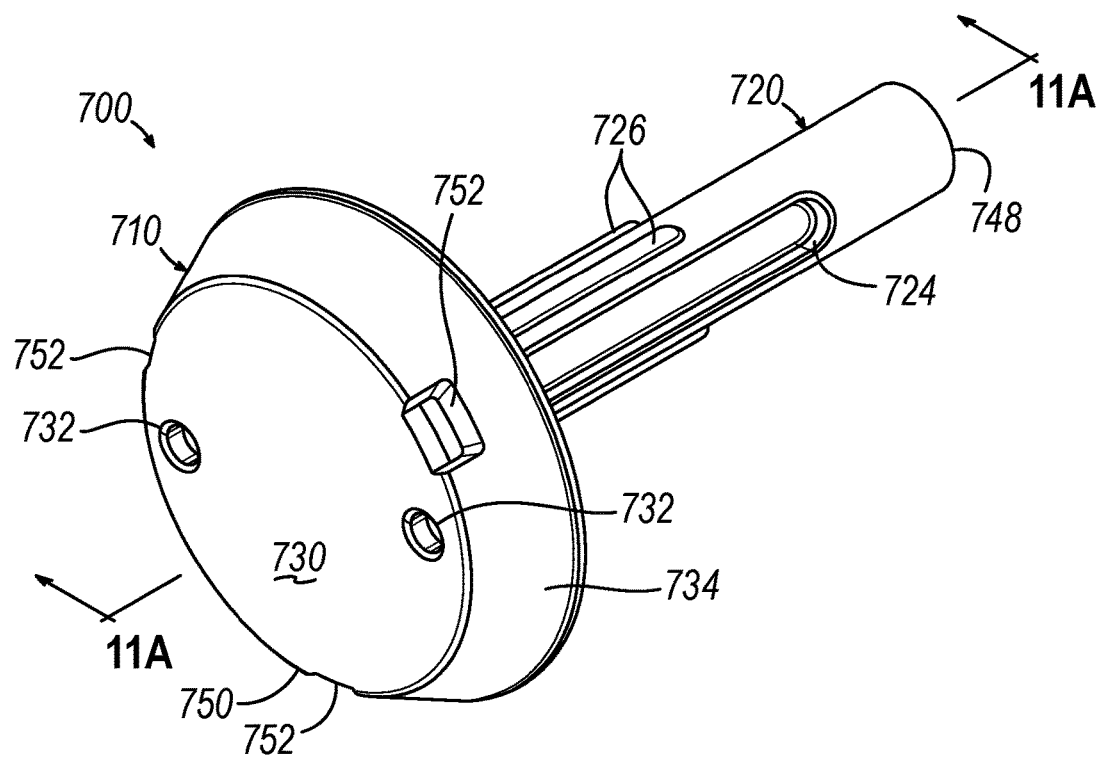
FIG. 11 depicts a perspective view of a second exemplary alternative anvil after forming a second exemplary head together with a second exemplary alternative shank, where the anvil may be incorporated into the circular surgical stapler of FIG. 1.
Figure 12:
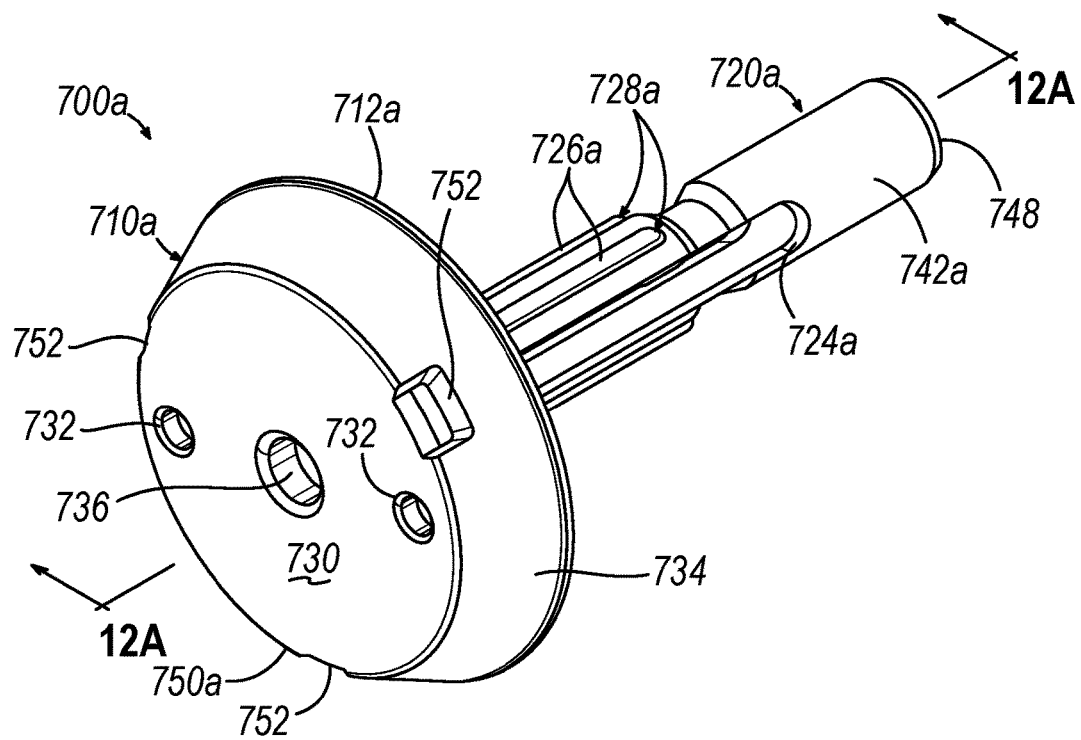
FIG. 12 depicts a perspective view of the anvil of FIG. 11 after a manufacturing step.
Figure 13:
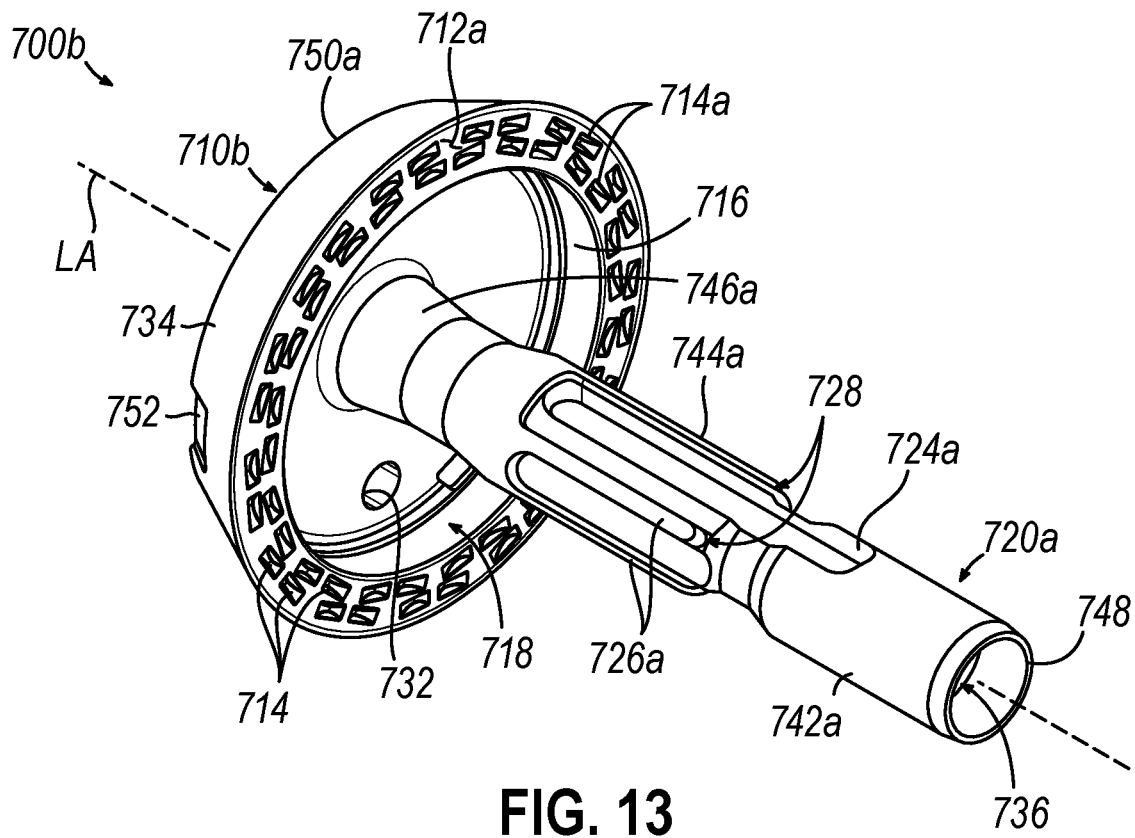
FIG. 13 depicts a perspective view of the anvil of FIG. 12 after another manufacturing step.
Figure 14:
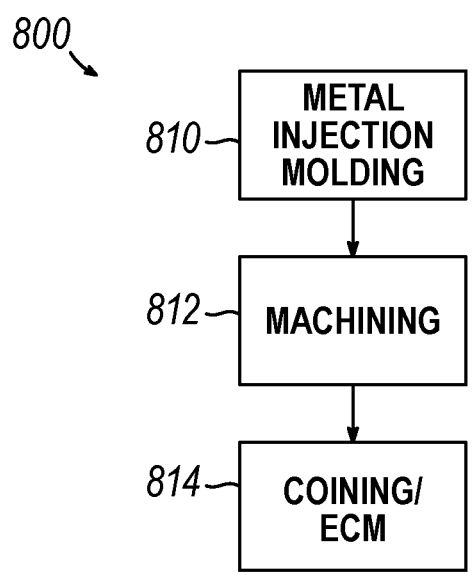
FIG. 14 depicts a diagrammatic view of an exemplary method of manufacturing the anvil of FIG. 13 that may be incorporated into the circular stapler of FIG. 1.

FIGS. 11-13 show a second exemplary alternative anvil (700, 700a, 700b) in various manufacturing stages, where anvil (700b) may be incorporated into instrument (10) of FIG. 1 in place of anvil (400, 500b) described above, and FIG. 14 shows an exemplary method of manufacturing anvil (700b). Similar to anvil (500), anvil (700) includes a head (710) and a shank (720). Similar to head (510), head (710) includes a proximal surface (712), an inner edge (716), an annular recess (718), a distal outer surface (730), a tapered portion (734). Similar to shank (520), shank (720) includes a bore (722), lateral openings (724), a set of longitudinally extending splines (726), a proximal portion (742), a central portion (744), and a distal portion (746).

Figure 11A:
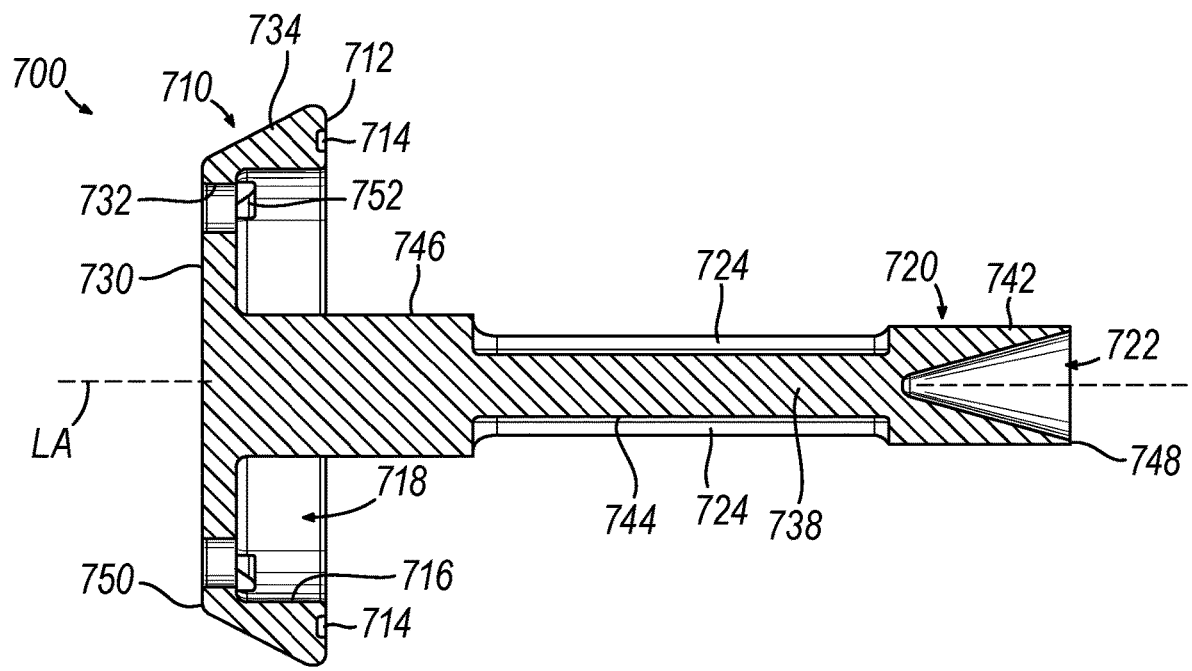
FIG. 11A depicts a sectional view of the anvil of FIG. 11, taken along line 11A-11A of FIG. 11.
Figure 12A:
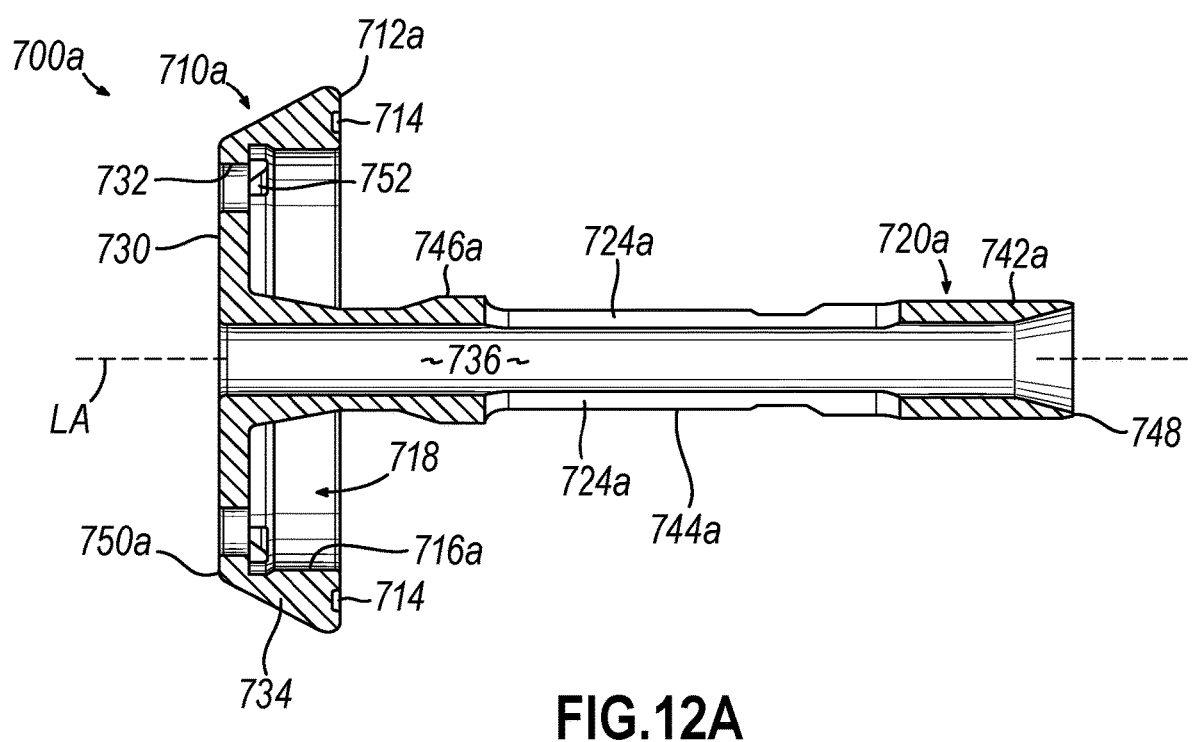
FIG. 12A depicts a sectional view of the anvil of FIG. 12, taken along line 12A-12A of FIG. 12.

At step (810), method (800) includes forming head (710) and shank (720) using at least one metal injection molding process to produce anvil (700) shown and described above with reference to FIGS. 11 and 11A. Similar to anvil (500), head (710) may be simultaneously formed with shank (720) using the same metal injection molding process. Unlike anvil (500) shown and described with reference to FIGS. 7-9, anvil (700) includes annular array of staple forming pockets (714) formed in head (710) of anvil (700) during the metal injection molding process. For example, staple forming pockets (714) may be formed simultaneously with head (710) during the metal injection molding process. Staple forming pockets (714) are shown schematically in FIGS. 11A and 12A. In this version, a locking feature (752) may be used to retain a washer (not shown but similar to washer (417)). The shape and dimensions of anvil (700) may be optimized for the metal injection molding process. Similar to shank (520), shank (720) has a generally solid shape (738) except for bore (722) and recesses (732).

After forming head (710) and shank (720) using metal injection molding, at step (812), method (800) may include machining select portions of head (710a) and/or shank (720a) of anvil (800a). As shown by comparing the cross-sections of FIGS. 11A and 12A, a groove (740) similar to groove (540) may be machined into inner edge (716a), also referred to as an inner side wall of head (710a). Proximal, central, and distal portions (742a, 744a, 746a) of shank (720a) may benefit from subsequent machining to improve select dimensional tolerances. As shown in the cross-sectional view of FIG. 12A, a through bore (736) is machined into shank (720a) that extends completely through longitudinal axis (LA) of shank (720a). In other words, through bore (736) extends from a tapered proximal end (748) of shank (720a) to a distal end (750) of head (710a). Through bore (736) includes a portion of bore (722) formed through the metal injection molding process. Portions of splines (726a), such as lead in edges (728), and lateral openings (724a) may be machined into shank (720a) to improve dimensional tolerances.

At step (814), method (800) may include coining or electrochemically machining at least a portion of staple forming pockets (714a) into head (710b) of anvil (700b). Since staple forming pockets (714) are formed into head (710) of anvil (700) during the metal injection molding process, coining or electrochemically machining may produce a smoother surface and a denser surface than another portion (e.g., an outer portion) that was not coined or electrochemically machined. Selective coining or electrochemically machining of staple forming pockets is additionally shown and described in U.S. Pub. No. 2020/0205835, entitled "Anvil for Circular Surgical Stapler and Associated Method of Manufacture with MIM," published Jul. 2, 2020, and issued as U.S. Pat. No. 11,291,450 on Apr. 5, 2022, the disclosure of which is incorporated by reference herein. Similar to method (600), method (800) may optionally include electropolishing at least a portion of staple forming pockets (714, 714a). Similar to method (600), method (800) may optionally include magnetically deburring or bead blasting at least head (710, 710a, 710b) as described above.

C. Third Exemplary Alternative Anvil and Method of Manufacturing

FIGS. 15-21 show a third exemplary alternative anvil (900, 900a) in various manufacturing stages where anvil (900a) may be incorporated into instrument (10) of FIG. 1 in place of anvil (400, 500b, 700b) described above, and FIG. 22 shows an exemplary method (1000) of manufacturing anvil (900a). Similar to anvils (400, 500, 700), anvil (900) includes a head (910) and a shank (920). Unlike anvils (400, 500, 700), head (910) is not integrally formed together with shank (920). Similar to head (510, 710), head (910) includes a proximal surface (912), an inner edge (916), an annular recess (918), a distal outer surface (930), and a tapered portion (934). Similar to shank (420, 520, 720), shank (920) includes a bore (922), lateral openings (924), a set of longitudinally extending splines (926), a proximal portion (942), a central portion (944), and a distal portion (946).

Figure 15:
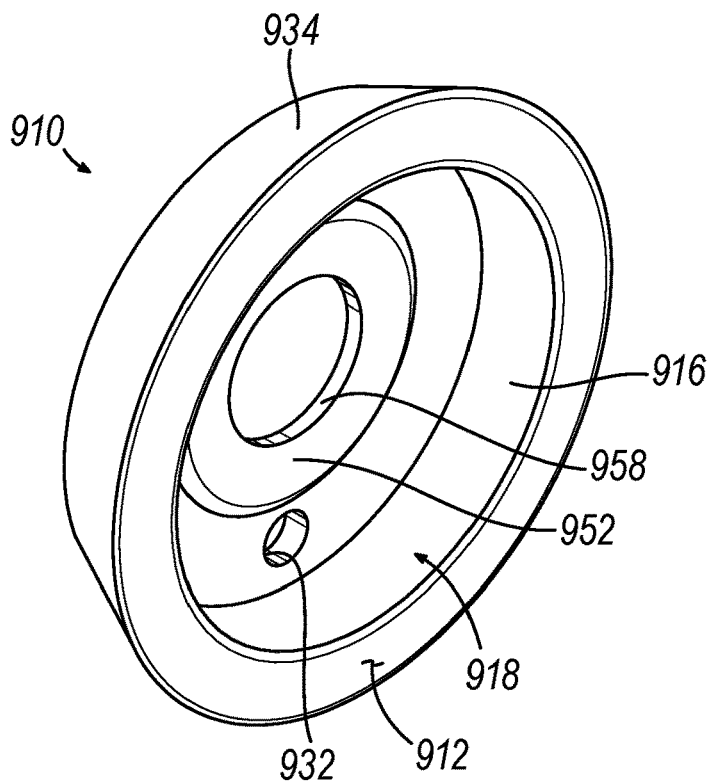
FIG. 15 depicts a perspective view of a third exemplary alternative head for a third exemplary alternative anvil.
Figure 16:
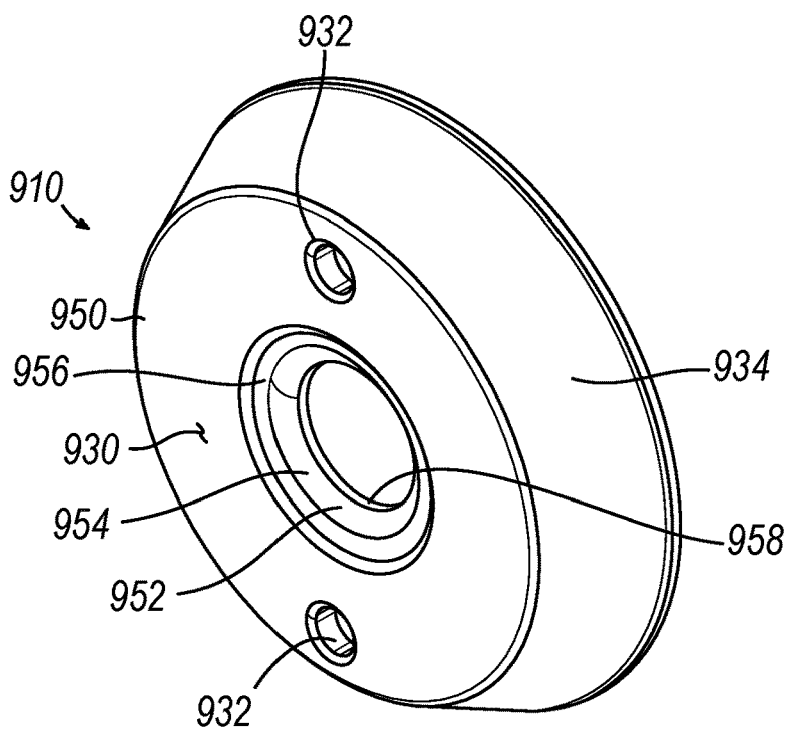
FIG. 16 depicts another perspective view of the head of FIG. 15.

Unlike heads (410, 510, 710), head (910) includes a recessed portion (952) that extends proximally from a distal outer surface (930) as shown in FIGS. 15-16. Recessed portion (952) includes a recessed surface (954) surrounded by an annular wall (956), with an aperture (958) extending through recessed surface (954) that is configured to receive shank (920). Recessed portion (952) of head (910) extends proximally from distal outer surface (950). Recessed surface (954) is surrounded by wall (956), with aperture (958) extending through recessed surface (954). As shown, aperture (958) is concentric to both distal outer surface (930) and recessed surface (954); however, other positionings of aperture (958) relative to distal outer surface (930) and recessed surface (954) are also envisioned.

Figure 17:
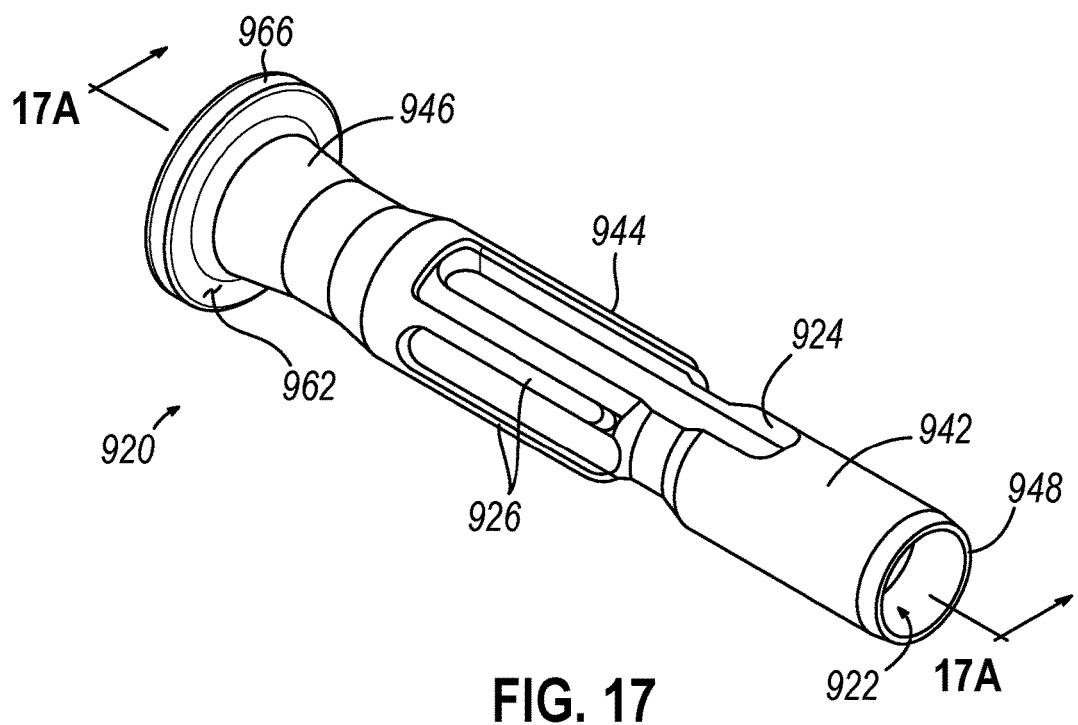
FIG. 17 depicts a perspective view of a third exemplary alternative shank for the third exemplary alternative anvil.
Figure 17A:
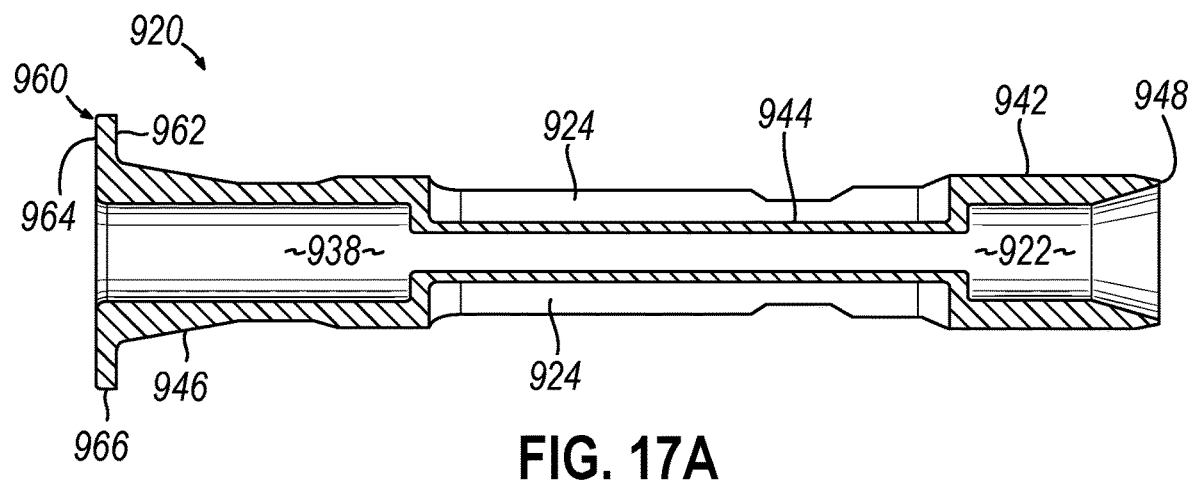
FIG. 17A depicts a sectional view of the shank of FIG. 17, taken along line 17A-17A of FIG. 17.
Figure 18:
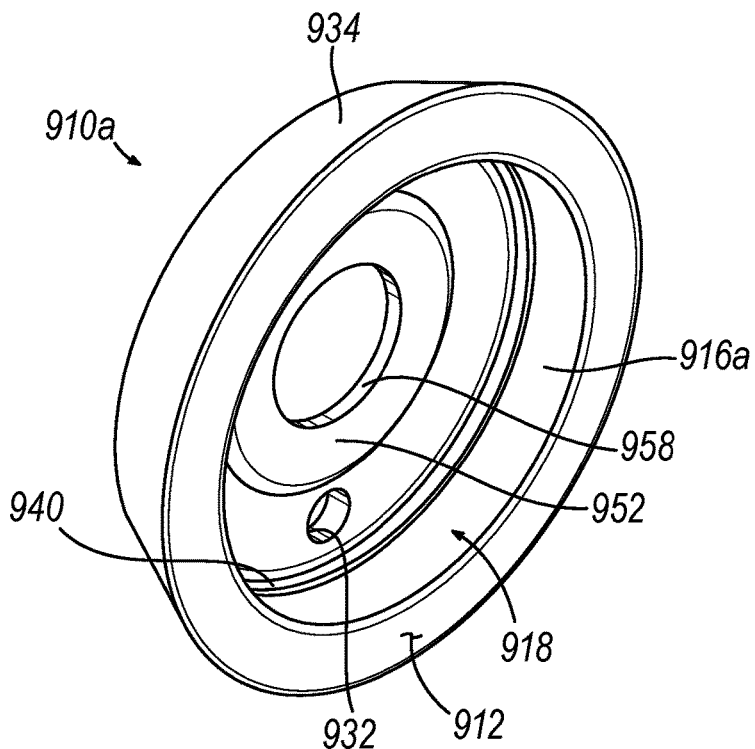
FIG. 18 depicts a perspective view of the head of FIG. 15 after a manufacturing step.
Figure 19:
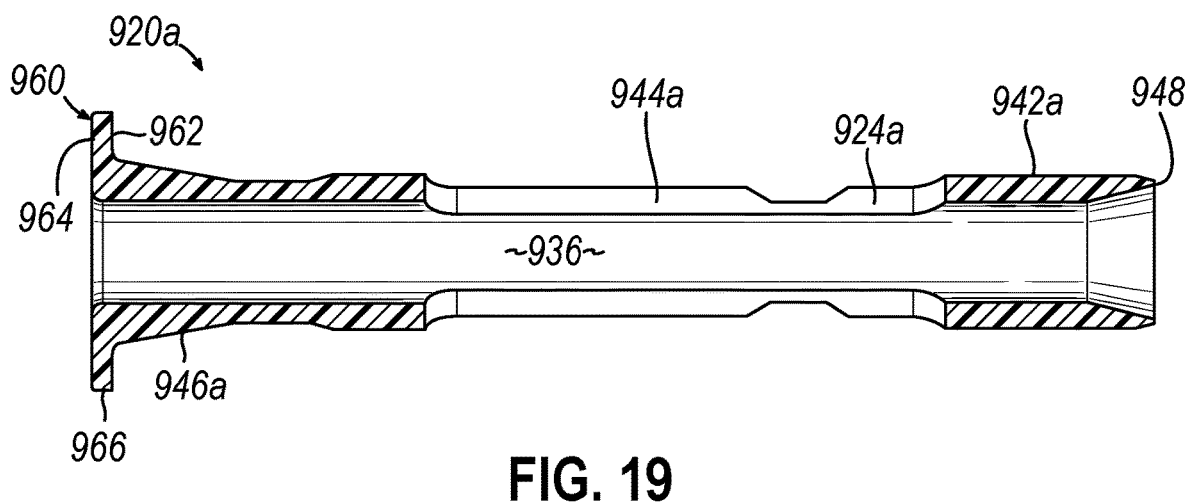
FIG. 19 depicts a sectional view of the shank of FIG. 17 after another manufacturing step.

Unlike shanks (420, 520, 720), as shown in FIG. 17-17A, shank (920) includes a flange (960) extending radially outward from distal portion (946) of shank (920). Flange (960) includes opposing proximal and distal surfaces (962, 964). Aperture (958) is configured to receive shank (920) therethrough. Recessed portion (952) is sized and configured to receive flange (960) of shank (920).

At step (1010), method (1000) includes forming head (910) and shank (920) using at least one metal injection molding process to produce head (910) shown in FIG. 15 and shank (920) shown in FIG. 16. Head (910) and shank (920) may be separately formed using separate metal injection molding processes. For example, head (910) may be formed separately from shank (920) using a first metal injection molding process, and shank (920) may be separately formed from head (910) using a second metal injection molding process. The shape and dimensions of anvil (900) may be optimized for the metal injection molding process. Unlike shanks (520, 720), as shown in FIG. 17A, bore (922) includes a narrow portion (938) extending along longitudinal axis (LA). In other words, bore (922) has a non-uniform width, with distal portion (946) of shank (920) having a different width than central portion (944).

After forming head (910) and shank (920) using the metal injection molding process, at step (1012), method (1000) may include machining select portions of head (910a) and/or shank (920a). As shown by comparing the perspective views of FIGS. 15 and 18, a groove (940) (similar to groove (740)) may be machined into inner edge (916a), also referred to as an inner side wall of head (910a). Proximal, central, and distal portions (942a, 944a, 946a) of shank (920a) may benefit from subsequent machining to improve select dimensional tolerances. A through bore (936) may be machined (e.g., using a drilling process) into shank (920a) so that through bore (936) extends completely through shank (920a). Portions of splines (926a), such as lead in edges (928), and lateral openings (924a) may be machined into shank (920a) to improve dimensional tolerances. Staple forming pockets (914) may be formed at step (1012) through machining or at step (1016) through coining and/or electrochemically machining.

Figure 20:
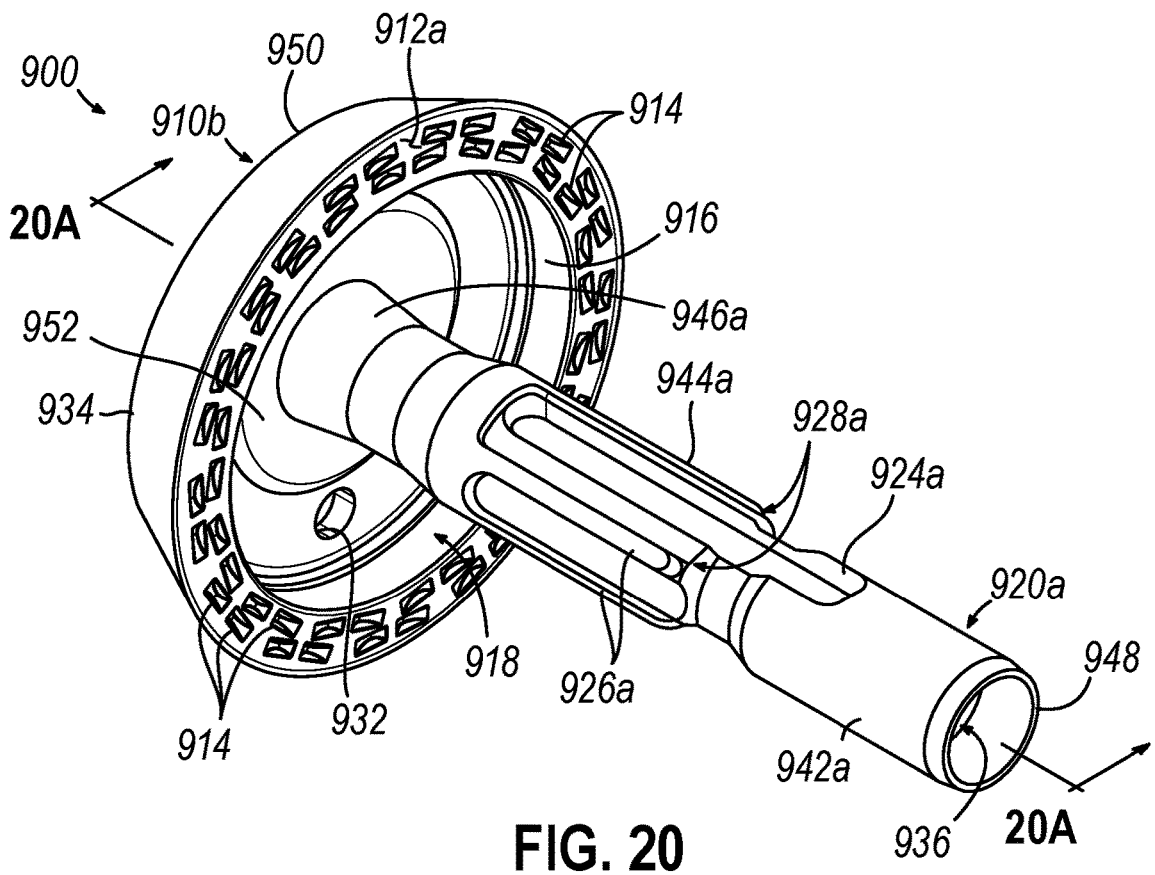
FIG. 20 depicts a perspective view of the anvil that includes the head of FIG. 24 and the shank of FIG. 25 after another manufacturing step.
Figure 20A:
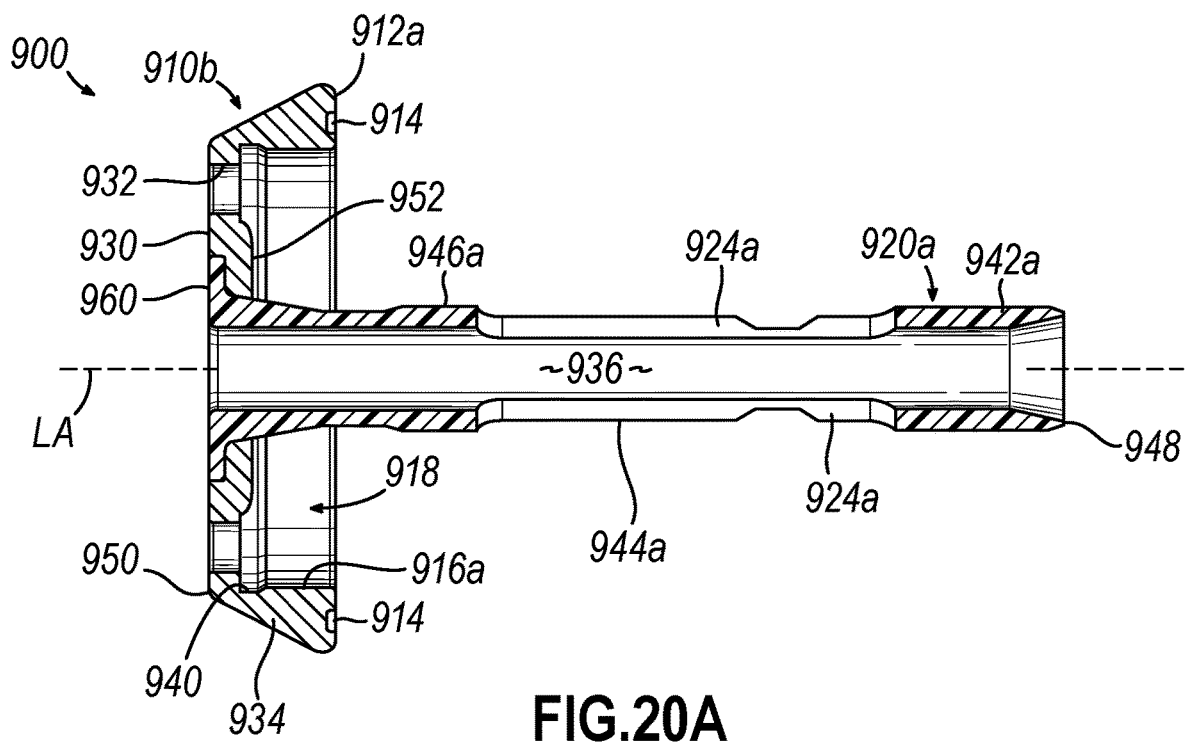
FIG. 20A depicts a sectional view of the anvil of FIG. 20, taken along line 20A-20A of FIG. 20.

At step (1014), method (1000) includes coupling head (910a) and shank (920a) together that were separately formed. In some versions, step (1014) may be performed before or during step (1012). Tapered proximal end (948) of shank (920a) is inserted though aperture (958) of head (910). Recessed portion (952) is sized and configured to receive flange (960) of shank (920a). As shown in FIG. 20A, recessed surface (954) of recessed portion (952) is in direct contact with proximal surface (962) of flange (960) once head (910a) is coupled with shank (920a). Recessed portion (952) of head (910) may be in direct contact with proximal surface (962) of flange (960) once head (910a) is coupled with shank (920a). The depth of recessed portion (952) may be about the same as the thickness of flange (960). However, the depth of recessed portion (952) and/or the thickness of flange (960) may vary.

Figure 21:
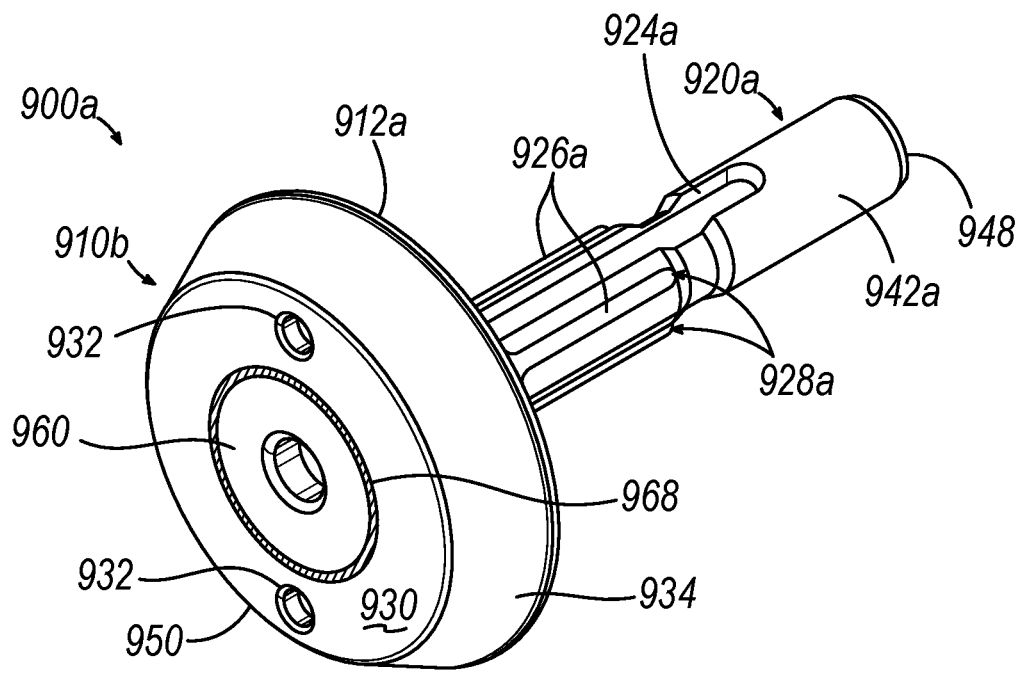
FIG. 21 depicts another perspective view of the anvil of FIG. 20.
Figure 22:
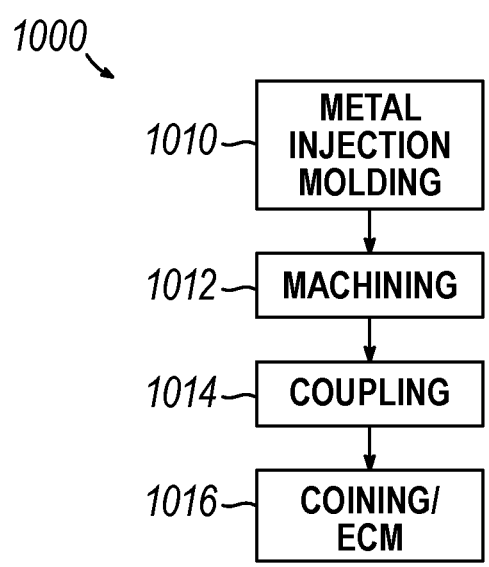
FIG. 22 depicts a diagrammatic view of an exemplary method of manufacturing the anvil of FIG. 21 that may be incorporated into the circular surgical stapler of FIG. 1.

As shown in FIG. 21, an outer perimeter (966) of flange (960) of shank (920a) may be welded together with head (910b) using a continuous weld (968) to secure head (910b) and shank (920a) together. One such suitable welding process is laser welding that is used to join together metals or thermoplastics using a laser beam to form a weld. Laser welding may reduce, or altogether eliminate, subsequent manufacturing processes (e.g., grinding) to refine continuous weld (968). In some versions, continuous weld (968) may be optionally ground down so distal outer surface (930) of head (910b) is generally flush with distal surface of flange (960) after head (910b) is coupled with shank (920a). The device used to join head (910b) and shank (920a) together may have appropriate indexing capabilities in order to reliably and consistently achieve the proper angular positioning of head (910b) and shank (920a) to thereby provide precise and consistent positioning of splines (926a) in relation to staple forming pockets (914).

Similar to methods (600, 800), at step (1016), method (1000) may include coining and/or electrochemically machining staple forming pockets (914). Coining or electrochemically machining staple forming pocket (914) results in a smoother surface and a denser surface than another portion that was not coined or electrochemically machined. As shown in FIG. 20, proximal surface (912a) of head (910b) defines an annular array of staple forming pockets (914). In some versions, staple forming pockets (914) may be formed simultaneously with head (910b) during the metal injection molding process. Similar to methods (600, 800), method (1000) may optionally include electropolishing at least a portion of the annular array of staple forming pockets (914). Similar to methods (600, 800), method (1000) may optionally include magnetically deburring or bead blasting at least head (910b) of anvil (900a).

D. Fourth Exemplary Alternative Anvil and Exemplary Method of Manufacturing

FIGS. 23-27 show a fourth exemplary alternative anvil (1100, 1100a, 1100b) in various manufacturing stages where anvil (1100b) may be incorporated into instrument (10) of FIG. 1 in place of anvil (400, 500b, 700b, 900a) described above, and FIG. 28 shows an exemplary method of manufacturing anvil (1100b). Similar to anvils (500, 700, 900), anvil (1100) includes a head (1110) and a shank (1120) which are machined as head (1110a) and shank (1120a). Similar to head (910), head (1110) includes a proximal surface (1112), staple forming pockets (1114), an inner edge (1116), an annular recess (1118), a distal outer surface (1130), a tapered portion (1134), a recessed portion (1152), a recessed surface (1154), an annular wall (1156), and an aperture (1158). Similar to shank (920), shank (1120) includes a bore (1122), lateral openings (1124), a set of longitudinally extending splines (1126), a proximal portion (1142), a central portion (1144), and a distal portion (1146), a proximal end (1148), a flange (1160), and opposing proximal and distal surfaces (1162, 1164).

Figure 23:
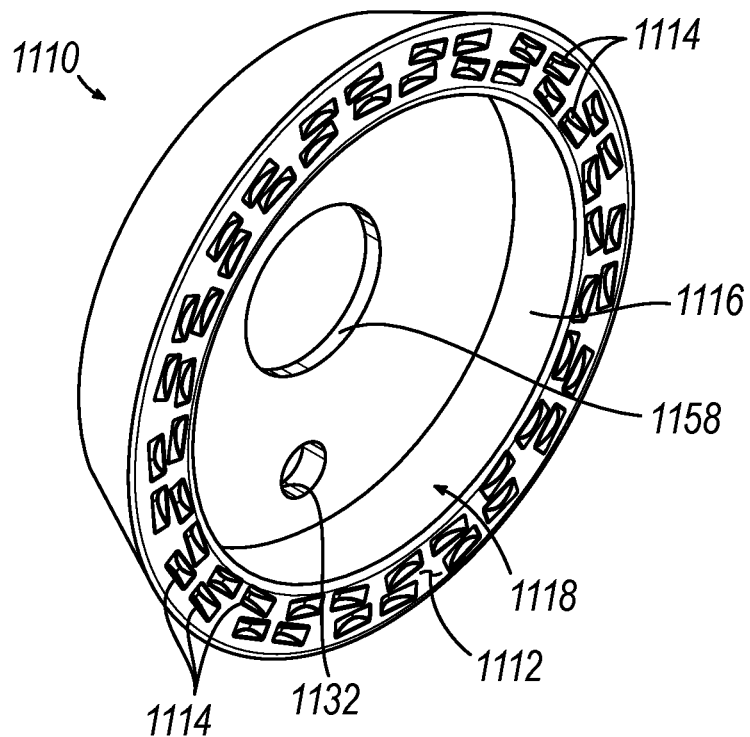
FIG. 23 depicts a perspective view of a fourth exemplary alternative head for a fourth exemplary alternative anvil.
Figure 24:
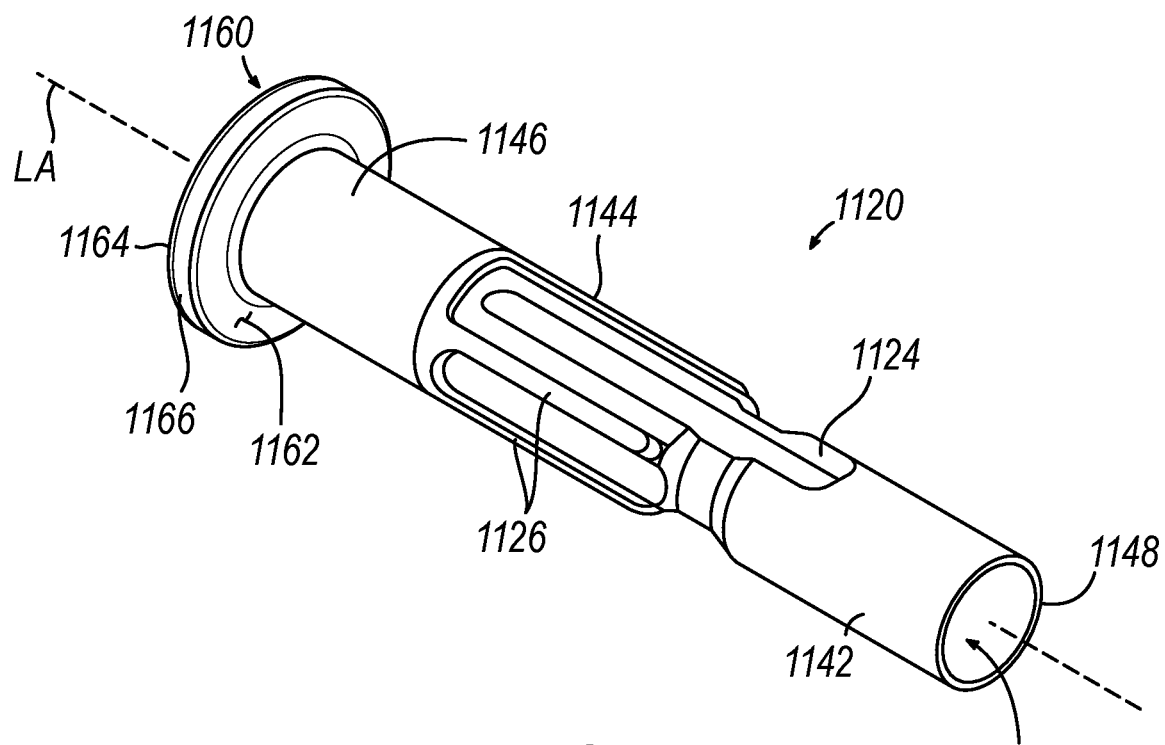
FIG. 24 depicts a perspective view of a fourth exemplary alternative shank for the fourth exemplary alternative anvil.
Figure 25:
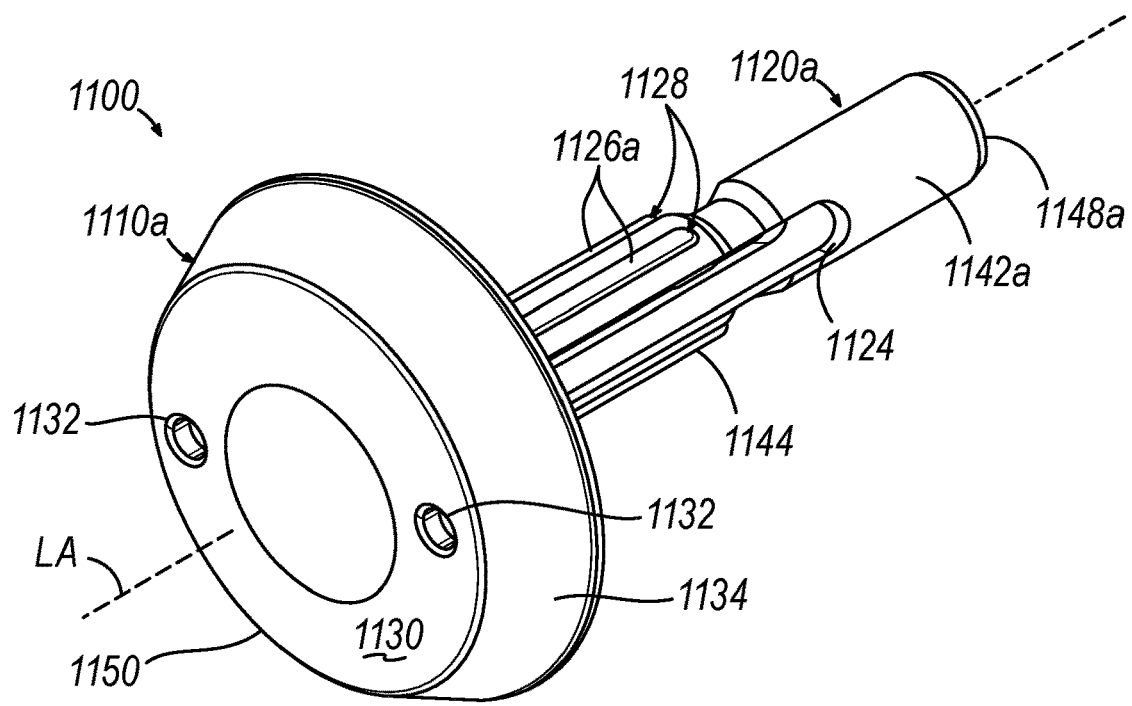
FIG. 25 depicts a perspective view of the anvil that includes the head of FIG. 23 and the shank of FIG. 24 after a manufacturing step.

At step (1210), method (1200) includes using at least one metal injection molding process to form head (1110) shown in FIG. 23 and shank (1120) shown in FIG. 24. Head (1110) and shank (1120) may be separately formed using metal injection molding processes. For example, head (1110) may be formed separately from shank (1120) using a first metal injection molding process, and shank (1120) may be separately formed from head (1110) using a second metal injection molding process. Unlike head (910), staple forming pockets (1114) are formed into head (1110) during the metal injection molding process. The shape and dimensions of anvil (1100) may be optimized for the metal injection molding process. Shank (1120) has a generally solid shape (1138) except for bore (1122) and recesses (1132).

Figure 26:
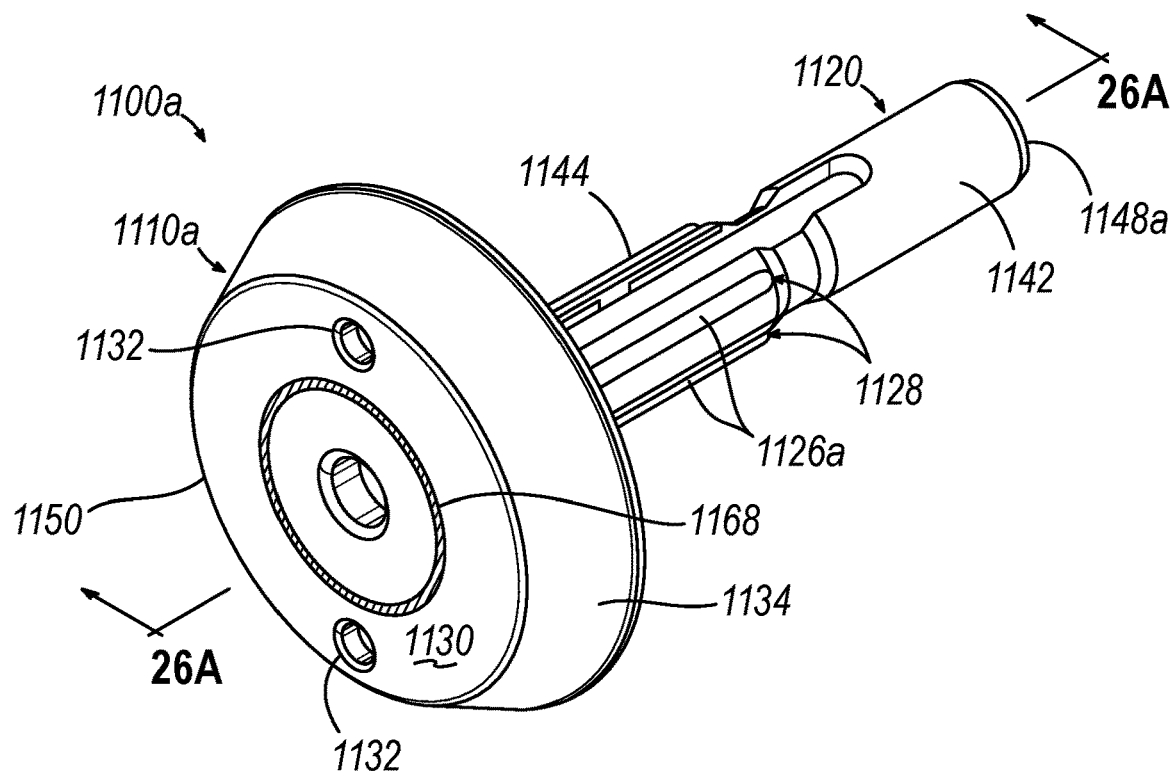
FIG. 26 depicts a perspective view of the anvil of FIG. 25 after another manufacturing step.

After forming head (1110) and shank (1120) using the metal injection molding process, at step (1212), method (1200) may include machining select portions of head (1110a) and/or shank (1120a). As shown in FIG. 26, a groove (1140) similar to groove (1140) may be machined into inner edge (1116a), also referred to as an inner side wall of head (1110a). Proximal, central, and distal portions (1142a, 1144a, 1146a) of shank (1120a) may benefit from subsequent machining to improve select dimensional tolerances. Regarding shank (1120a), a through bore (1136) is machined into shank (1120a) that extends completely through longitudinal axis (LA) of shank (1120a). Portions of splines (1126a), such as lead-in edges (1128) may be machined into shank (1120a) and lateral openings (1124a) may be refined to improve dimensional tolerances. Tapered proximal end (1148a) may also be machined.

Figure 26A:
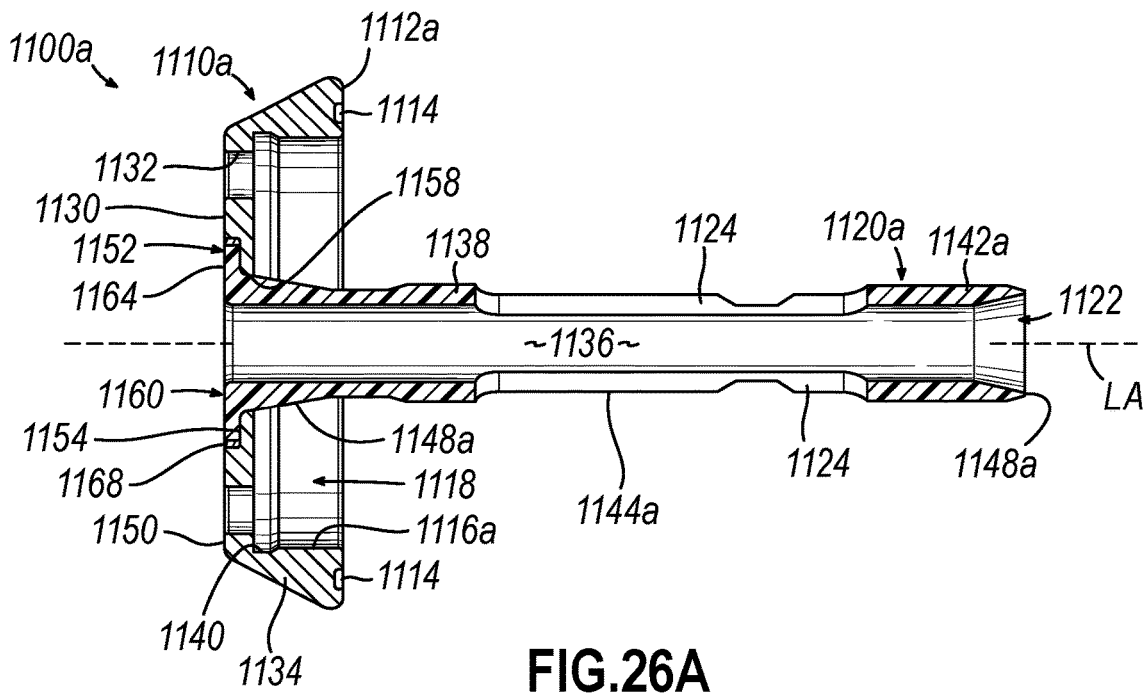
FIG. 26A depicts a sectional view of the shank of FIG. 26, taken along line 26A-26A of FIG. 26.

At step (1214), method (1200) includes coupling head (1110a) and shank (1120a) together that were separately formed and machined. In some versions, step (1214) may be performed before step (1212), so that head (1110a) and shank (1120a) may be coupled then machined. In some versions, an outer perimeter (1166) of flange (1160) may be welded together with head (1110a) using a continuous weld (1168) to secure head (1110a) and shank (1120a) together. As shown in FIG. 26A, recessed surface (1154) of recessed portion (1152) is in direct contact with proximal surface (1162) of flange (1160) once head (1110a) is coupled with shank (1120a). Distal outer surface (1130) of head (1110a) is generally flush with distal surface of flange (1160) after head (1110a) is coupled with shank (1120a).

Figure 27:
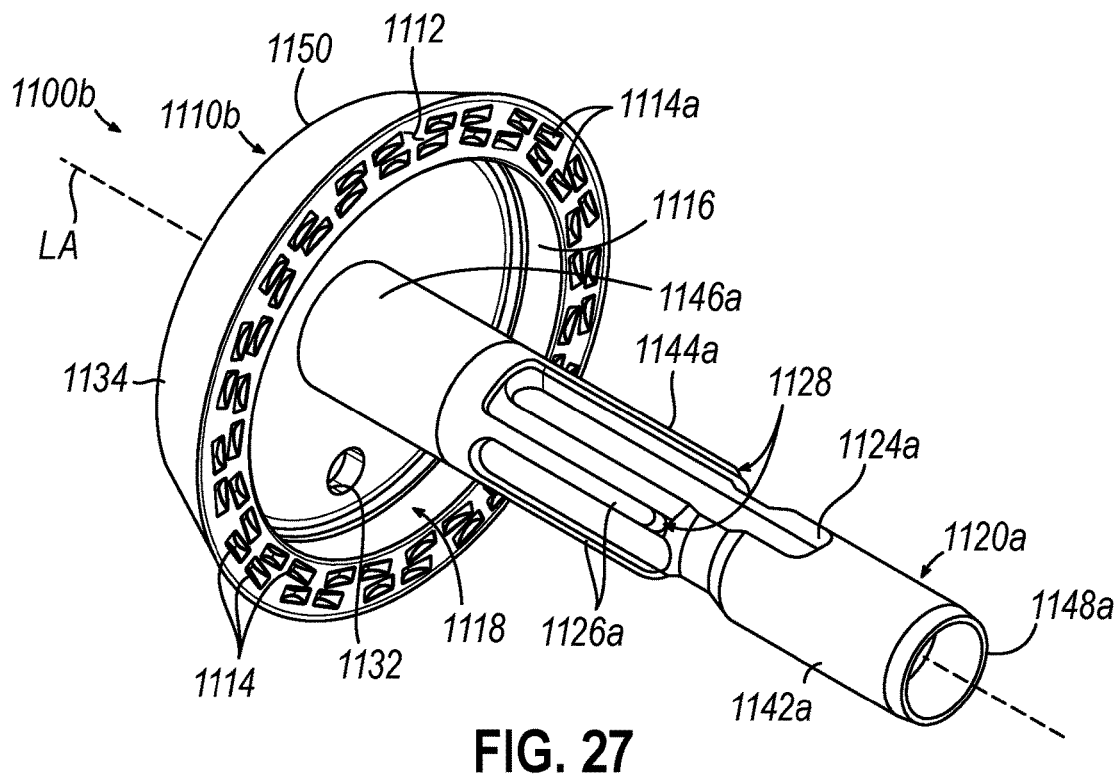
FIG. 27 depicts a perspective view of the anvil of FIG. 26 after another manufacturing step.
Figure 28:
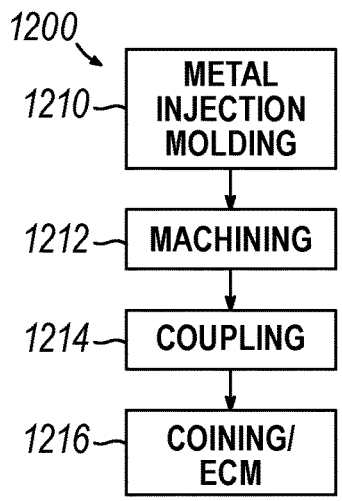
FIG. 28 depicts a diagrammatic view of an exemplary method of manufacturing the anvil of FIG. 27 that may be incorporated into the circular surgical stapler of FIG. 1.

Similar to step (814), at step (1216), method (1200) may include coining or electrochemically machining at least a portion of staple forming pockets (1114a) of head (1110a) (see FIG. 27). Since staple forming pockets (1114) are formed into head (1110) during the metal injection molding process, at least a portion of staple forming pocket (1114a) may be coined or electrochemical machined. The portion of staple forming pocket (1114a) subsequently coined or electrochemically machined produces a smoother surface and a denser surface than another portion (e.g., an outer portion) that was not coined or electrochemically machined. In some versions, step (1216) may be performed before step (1214), so that head (1110a) and shank (1120a) may be coupled before being coined or electrochemically machined. Similar to method (600), method (1200) may optionally include electropolishing at least a portion of the annular array of staple forming pockets (1114). Similar to method (600), method (1200) may optionally include magnetically deburring or bead blasting at least head (1110a, 1110b) of anvil (1100a, 1100b).

E. Fifth Exemplary Alternative Anvil and Method of Manufacturing

FIGS. 29-32 show a fifth exemplary alternative anvil (1300, 1300a) in various manufacturing stages where anvil (1300a) may be incorporated into instrument (10) of FIG. 1 in place of anvil (500b, 700b, 900a, 1100b) described above, and FIG. 33 shows an exemplary method of manufacturing anvil (1300a). Similar to anvil (500, 700, 900, 1100), anvil (1300) includes a head (1310) and a shank (1320). Similar to head (1110), head (1310) includes a proximal surface (1312), staple forming pockets (1314), an inner edge (1316), an annular recess (1318), a distal outer surface (1330), a tapered portion (1334), a recessed portion (1352), a recessed surface (1354), an annular wall (1356), and an aperture (1358). Similar to shank (920), shank (1320) includes a bore (1322), lateral openings (1324), a proximal portion (1342), a central portion (1344), a distal portion (1346), a proximal end (1348), a flange (1360), and opposing proximal and distal surfaces (1362, 1364).

Figure 29:
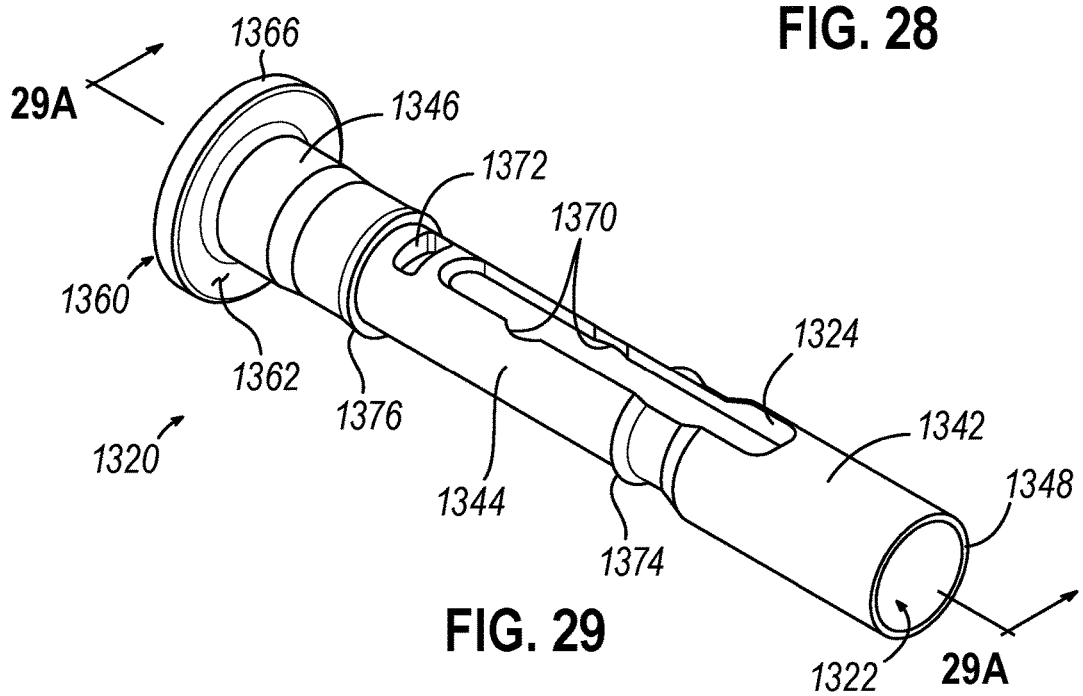
FIG. 29 depicts a perspective view of a fifth exemplary shank for a fifth exemplary alternative anvil.
Figure 29A:
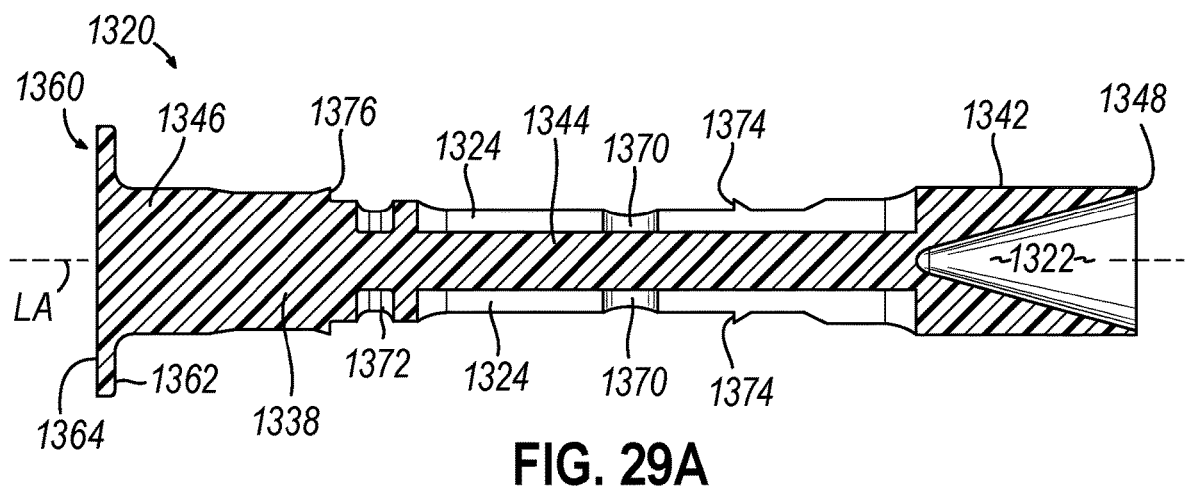
FIG. 29A depicts a sectional view of the shank of FIG. 30, taken along line 30A-30A of FIG. 30.
Figure 30:
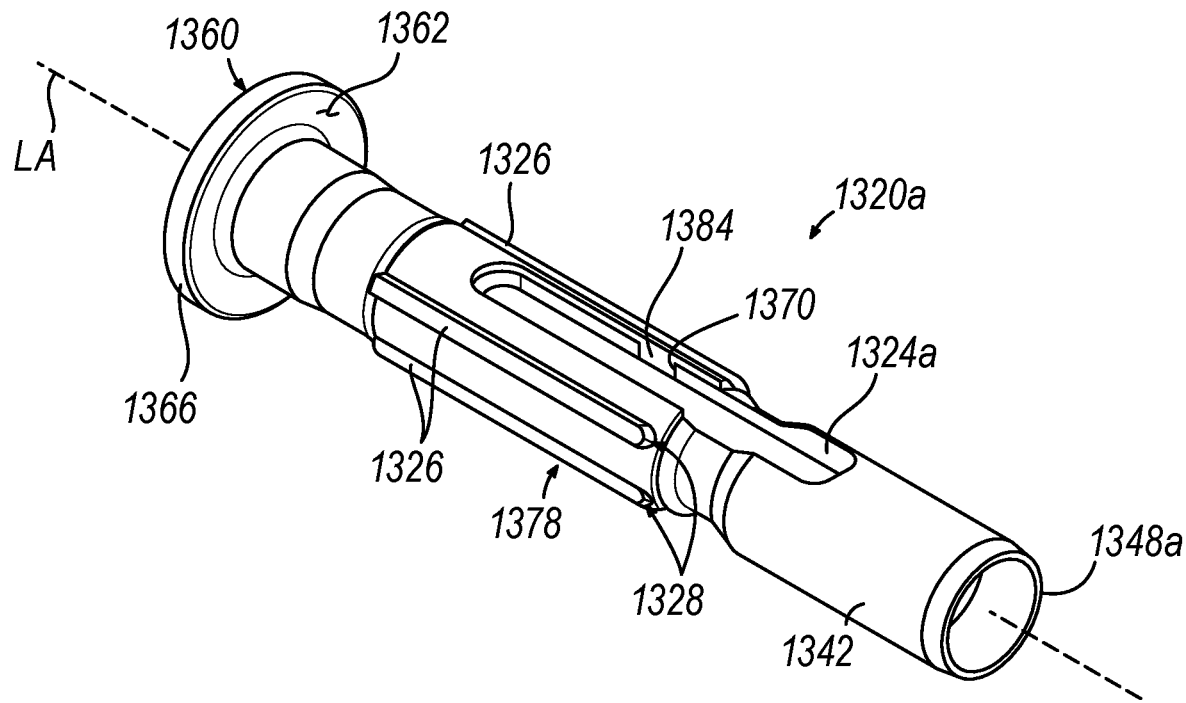
FIG. 30 depicts a sectional view of the shank of FIG. 30 coupled with an insert after a manufacturing step.

At step (1410), method (1400) includes using at least one metal injection molding process to form head (1310) and shank (1320). Metal injection molded head (1310) may be similar to head (910) that omits staple forming pockets (914)

or head (1110) that includes staple forming pockets 1114) formed using metal injection molding. Head (1310) and shank (1320) may be separately formed using metal injection molding processes. For example, head (1310) may be formed separately from shank (1320) using a first metal injection molding process, and shank (1320) may be separately formed from head (1310) using a second metal injection molding process. The shape and dimensions of anvil (1300) may be optimized for the metal injection molding process. As shown in FIG. 29A, shank (1320) has a generally solid shape (1338) except for bore (1322) and one or more recessed portions, shown as proximal and distal recessed portions (1370, 1372). Proximal and distal recessed portions (1370, 1372) are configured to subsequently receive an insert (1378) as described below.

After forming head (1310) and shank (1320) using the metal injection molding process, at step (1412), method (1400) may include machining select portions of head (1310) and/or shank (1320a). Head (1310) includes a groove (1340) similar to groove (1140), machined into inner edge (1316). Proximal, central, and distal portions (1342a, 1344a, 1346a) of shank (1320a) may benefit from subsequent machining to improve select dimensional tolerances. Regarding shank (1320a), a through bore (1336) is machined into shank (1320a) that extends completely through longitudinal axis (LA) of shank (1320). Lateral openings (1324a) and distal end (1342a) may also be machined to improve dimensional tolerances.

At step (1416), method (1400) includes injection molding an insert (1378) onto shank (1320a). Unlike anvils (400, 500, 700, 900, 1100), anvil (1300) includes insert (1378) coupled with central portion (1344a) of shank (1320a). In some versions, insert (1378) is formed of a polymeric material onto shank (1320a), such that step (1416) includes plastic injection molding onto shank (1320a). Unlike the previously described shanks, insert (1378) includes a plurality of splines (1326). Splines (1326) are configured to align with features (gaps between splines) of instrument (10). Insert (1378) circumferentially surrounds at least a portion of central portion (1344a) of shank (1320a). Splines (1326a) include lead-in edges (1328). Shank (1320a) includes proximal and distal retaining portions (1374, 1376) configured to retain insert (1378) and prevent insert (1378) from moving proximally or distally relative to shank (1320a). Using insert (1378) may reduce, or altogether eliminate, machining of shank (1320) into shank (1320a). Insert (1378) includes proximal and distal inwardly facing portions (1380, 1382). As shown, proximal inwardly facing portion (1380) is coupled with proximal recessed portion (1370) and distal inwardly facing portion (1382) is coupled with distal recessed portion (1372). Distal end (1348) may be machined to include a tapered distal; end (1348a).

Figure 31:
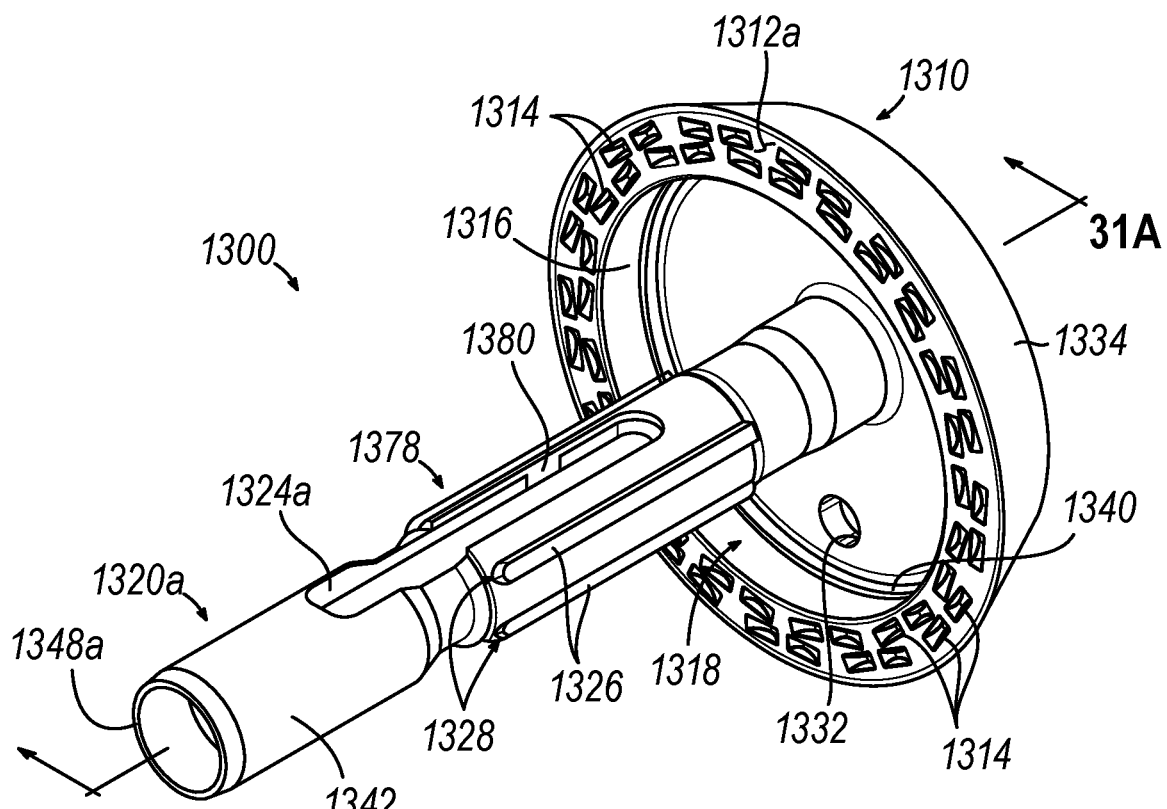
FIG. 31 depicts a perspective view of the fifth exemplary alternative anvil that includes a fifth exemplary alternative head.
Figure 31A:
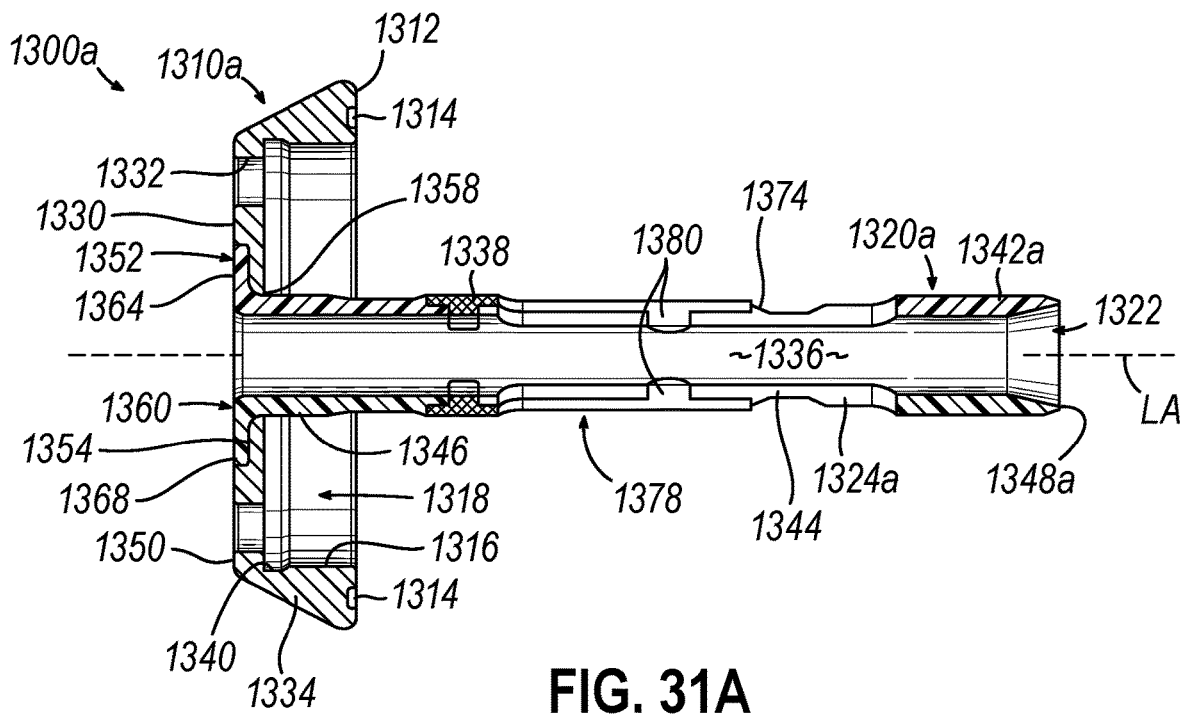
FIG. 31A depicts a sectional view of the anvil of FIG. 31, taken along line 31A-31A of FIG. 31.
Figure 32:
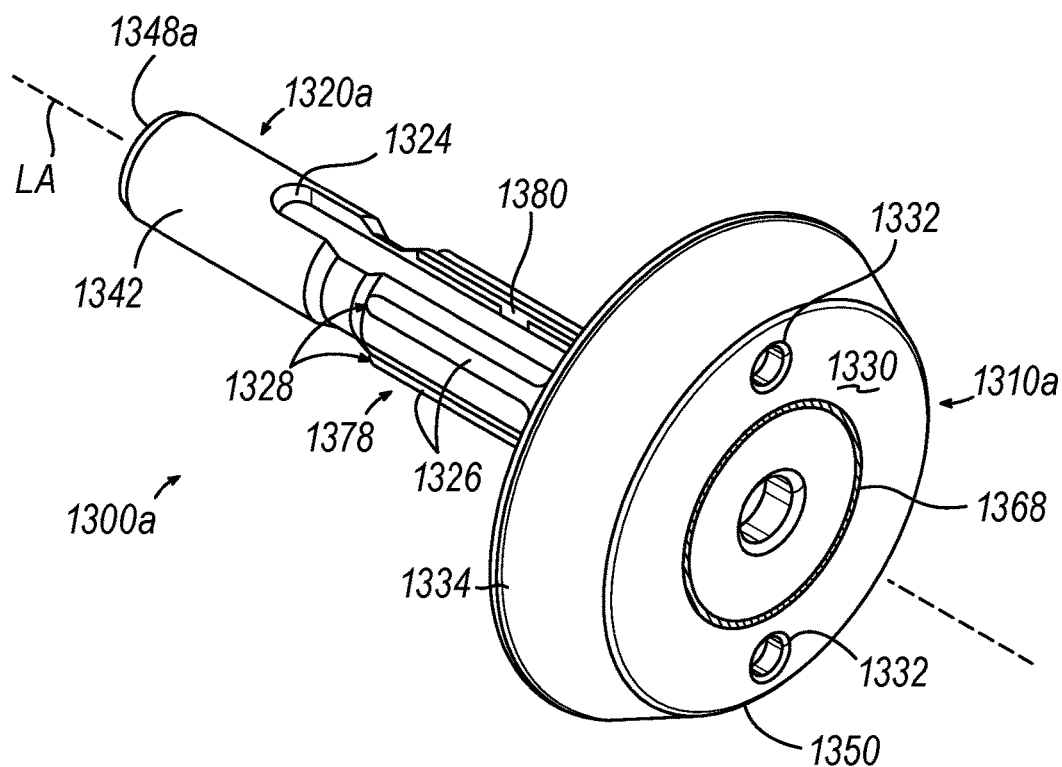
FIG. 32 depicts a perspective view of the anvil of FIG. 31 after another manufacturing step.
Figure 33:
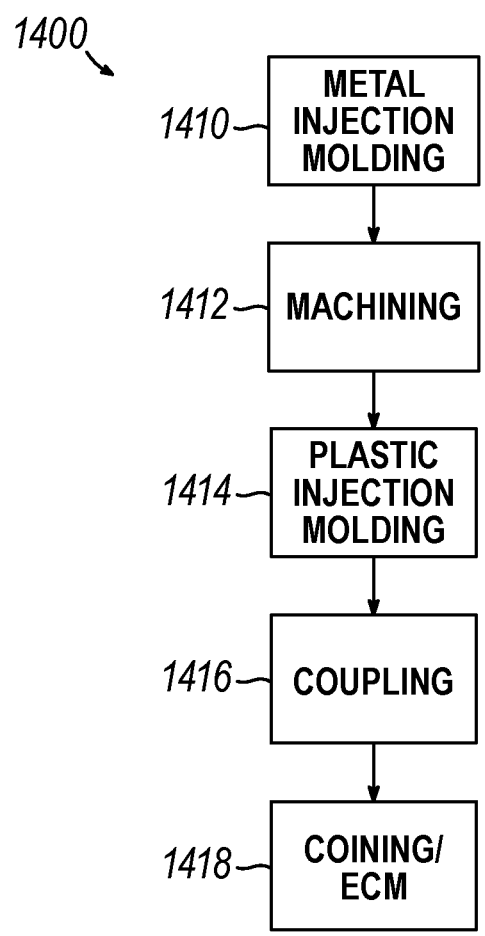
FIG. 33 depicts a diagrammatic view of an exemplary method of manufacturing the anvil of FIG. 32 that may be incorporated into the circular surgical stapler of FIG. 1.

At step (1416), method (1400) includes coupling head (1310) and shank (1320a) together that were separately formed. As shown in FIG. 31A, recessed surface (1354) of recessed portion (1352) is in direct contact with proximal surface (1354) of flange (1360) once head (1310) is coupled with shank (1320a). Distal outer surface (1330) of head (1310) is generally flush with distal surface of flange (1360) after head (1310) is coupled with shank (1320). In some versions, step (1414) may be performed before step (1412). In some versions, an outer perimeter (1366) of flange (1360) may be welded together with head (1310) using a continuous weld (1368) to secure head (1310) and shank (1320a) together. One such suitable welding process is laser welding that is used to join together metals or thermoplastics using a laser beam to form a weld. Laser welding may reduce or eliminate the need for subsequent manufacturing processes (e.g., grinding).

Similar to step (614), at step (1418), method (1400) may include coining or electrochemically machining staple forming pockets (1314) (shown schematically in FIG. 31A). In some versions, since staple forming pockets (1314) are formed into head (1310) of anvil (1300) during the metal injection molding process, a select portion of staple forming pockets (1314) may be coined or electrochemical machined. The portion of staple forming pocket (1314) subsequently coined or electrochemically machined results in a smoother surface and a denser surface than another portion (e.g., an outer portion) that was not coined or electrochemically machined. Similar to method (600), method (1400) may optionally include electropolishing at least a portion of the annular array of staple forming pockets (1314). Similar to method (600), method (1400) may optionally include magnetically deburring or bead blasting at least head (1310).

Those of ordinary skill in the art will understand that staples formed by anvil (500b, 700b, 900a, 1100b, 1300a) will have a three-dimensional profile, where the legs are angularly offset from a plane passing through a crown of the staple; in addition to being bent generally toward each other. By way of example only, the staples formed using anvil (500b, 700b, 900a, 1100b, 1300a) may have an appearance similar to at least some of the staples shown and described in U.S. Pat. No. 10,092,292, entitled "Staple Forming Features for Surgical Stapling Instrument," issued on Oct. 9, 2018, the disclosure of which is incorporated by reference herein. By way of further example only, the staples formed using anvil (500b, 700b, 900a, 1100b, 1300a) may have an appearance similar to at least some of the staples shown and described in U.S. Pat. Pub. No. 2018/0132849, entitled "Staple Forming Pocket Configurations for Circular Surgical Stapler Anvil," published May 17, 2018, now abandoned, the disclosure of which is incorporated by reference herein. Additional features of anvils are disclosed in U.S. Pat. No. 10,709,452, entitled "Methods and Systems for Performing Circular Stapling," issued Jul. 14, 2020; U.S. Pub. No. 2015/0083772 published Mar. 26, 2015, now abandoned; U.S. Pat. No. 9,907,552, issued Mar. 6, 2018; U.S. Pat. No. 10,478,189, entitled "Method of Applying an Annular Array for Staples to Tissue," issued Nov. 19, 2019; U.S. Pub. No. 2018/0132849 published May 17, 2018, now abandoned; U.S. Pat. No. 10,729,444, entitled "Liquid-Immune Trigger Circuit for Surgical Instrument," issued Aug. 4, 2020; and U.S. Pat. No. 10,695,068, entitled "Hysteresis Removal Feature in Surgical Stapling Instrument," issued Jun. 30, 2020, the disclosures of which are incorporated by reference herein.

In addition to or in lieu of the foregoing, anvil (500, 700, 900, 1100, 1300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing an anvil of a circular surgical stapler, wherein the anvil includes a head and a coupling feature that extends proximally from the head, the method comprising: (a) forming each of the head and the coupling feature using at least one metal injection molding process; and (b) after forming the coupling feature, machining a through bore into the coupling feature that extends completely through the coupling feature along a longitudinal axis of the coupling feature.

Example 2

The method of Example 1, wherein the coupling feature includes a shank, wherein machining the through bore further comprises machining the through bore into the shank so that the through bore extends completely through the shank along the longitudinal axis.

Example 3

The method of Example 2, further comprising forming the head simultaneously with the shank using the same metal injection molding process.

Example 4

The method of Example 2, wherein forming the head and the shank using at least one metal injection molding process further comprises forming the head separate from the shank using a first metal injection molding process, and forming the shank separate from the head using a second metal injection molding process, the method further comprising coupling together the head and the shank that were separately formed.

Example 5

The method of any one or more of Examples 2 through 4, further comprising machining a plurality of splines into the shank which are configured to align with features of the circular surgical stapler.

Example 6

The method of any one or more of Examples 2 through 5, wherein forming the shank further comprises forming a flange extending radially outward from a distal end of the shank using the at least one metal injection molding process.

Example 7

The method of Example 6, further comprising welding an outer perimeter of the flange with the head to secure the shank and head together.

Example 8

The method of any one or more of Examples 2 through 7, further comprising plastic injection molding an insert formed of a polymeric material onto the shank.

Example 9

The method of any one or more of the preceding Examples, further comprising machining at least a portion of the head after forming the head using the metal injection molding process.

Example 10

The method of any one or more of the preceding Examples, further comprising after forming the head, machining a groove into an inner side wall of the head.

Example 11

The method of any one or more of the preceding Examples, further comprising magnetically deburring or bead blasting at least the head of the anvil.

Example 12

The method of any one or more of the preceding Examples, further comprising forming an annular array of staple forming pockets in the head.

Example 13

The method of Example 12, further comprising electropolishing at least a portion of the annular array of staple forming pockets.

Example 14

The method of any one or more of Examples 12 through 13, further comprising coining or electrochemical machining at least a portion of at least one staple forming pocket of the annular array of staple forming pockets.

Example 15

The method of any one or more of the preceding Examples, coupling the anvil with a trocar of the circular surgical stapler.

Example 16

A method of manufacturing an anvil of a circular surgical stapler, wherein the anvil includes a head and a coupling feature extending proximally from the head, the method comprising: (a) forming the head including an annular array of staple forming pockets using a first metal injection molding process; (b) forming the coupling feature using a second metal injection molding process; and (c) coupling a polymeric insert that includes a plurality of splines with the coupling feature, wherein the plurality of splines is configured to align with features of the circular surgical stapler.

Example 17

The method of Example 16, further comprising coining or electrochemical machining at least a portion of the annular array of staple forming pockets.

Example 18

The method of any one or more of Examples 16 through 17, wherein the coupling feature includes a shank, the method further comprising welding an outer perimeter of a flange of the shank with the head to secure the shank and the head together.

Example 19

A surgical instrument comprising: (a) a body; (b) a shaft extending distally from the body; (c) a stapling head assembly positioned at a distal end of the shaft, wherein the stapling head assembly includes: (i) a first coupling feature, (ii) at least one annular array of staples, and (iii) a staple driver, wherein the staple driver is operable to drive the at least one annular array of staples; and (d) an anvil configured to couple with the first coupling feature, wherein the anvil is further configured to deform the staples driven by the staple driver, wherein the anvil comprises: (i) a head that includes an annular array of staple forming pockets, and (ii) a second coupling feature coupled with the head and defining a longitudinal axis, wherein the second coupling feature includes a through bore extending completely through the second coupling feature along the longitudinal axis of the second coupling feature.

Example 20

The surgical instrument of Example 19, wherein the second coupling feature includes a shank that extends along the longitudinal axis, wherein the shank includes a flange, wherein the head includes a distal outer surface and a distal recessed portion that is disposed proximal to the distal outer surface, wherein the anvil further comprises a weld extending completely along an outer perimeter of the flange.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A method of manufacturing an anvil of a circular surgical stapler, wherein the anvil includes a head and a shank that extends proximally from the head, the method comprising:
   (a) simultaneously forming each of the head and the shank using the same metal injection molding process; and
   (b) after simultaneously forming each of the head and the shank using the same metal injection molding process, machining a through bore into the shank that extends completely through the shank along a longitudinal axis of the shank.

2. The method of claim 1, further comprising machining a plurality of splines into the shank which are configured to align with features of the circular surgical stapler.

3. The method of claim 1, wherein forming the shank further comprises forming a flange extending radially outward from a distal end of the shank using the at least one metal injection molding process.

4. The method of claim 1, further comprising plastic injection molding an insert formed of a polymeric material onto the shank.

5. The method of claim 1, further comprising machining at least a portion of the head after forming the head.

6. The method of claim 1, further comprising after forming the head, machining a groove into an inner side wall of the head.

7. The method of claim 1, further comprising magnetically deburring or bead blasting at least the head of the anvil.

8. The method of claim 1, further comprising forming an annular array of staple forming pockets in the head.

9. The method of claim 8, further comprising electropolishing at least a portion of the annular array of staple forming pockets.

10. The method of claim 8, further comprising coining or electrochemical machining at least a portion of at least one staple forming pocket of the annular array of staple forming pockets.

11. The method of claim 1, coupling the anvil with a trocar of the circular surgical stapler.

12. A method of manufacturing an anvil of a circular surgical stapler, wherein the anvil includes a head and a coupling feature extending proximally from the head, the method comprising:
(a) forming the head including an annular array of staple forming pockets using a first metal injection molding process;
(b) forming using a second metal injection molding process; and
(c) coupling a polymeric insert that includes a plurality of splines with the coupling feature, wherein the plurality of splines is configured to align with features of the circular surgical stapler.

13. The method of claim 12, further comprising coining or electrochemical machining at least a portion of the annular array of staple forming pockets.

14. The method of claim 12, wherein the coupling feature includes a shank, the method further comprising welding an outer perimeter of a flange of the shank with the head to secure the shank and the head together.

15. A method of manufacturing an anvil of a circular surgical stapler, wherein the anvil includes a head and a shank that extends proximally from the head, the method comprising:
(a) forming the head and the shank simultaneously or sequentially using first and second metal injection molding processes;
(b) after forming at least the shank, machining a through bore into the shank that extends completely through the shank along a longitudinal axis of the shank; and
(c) coupling the head and the shank together before or after machining the through bore so that the through bore extends completely through an entirety of the anvil and the head circumferentially surrounds the through bore.

16. The method of claim 15, further comprising welding an outer perimeter of the flange with the head to secure the shank and head together.

17. The method of claim 15, wherein forming the head and the shank simultaneously or sequentially using the first and second injection molding processes further comprises forming the head separate from the shank using the first metal injection molding process, and forming the shank separate from the head using the second metal injection molding process after forming the head.

18. The method of claim 15, further comprising plastic injection molding an insert formed of a polymeric material onto the shank.

19. The method of claim 15, further comprising after forming the head, machining a groove into an inner side wall of the head.

20. The method of claim 15, further comprising magnetically deburring or bead blasting at least the head of the anvil.

\* \* \* \* \*